US010307150B2

(12) United States Patent
Kahook et al.

(10) Patent No.: US 10,307,150 B2
(45) Date of Patent: Jun. 4, 2019

(54) OCULAR TISSUE EXPANSION RING

(71) Applicant: THE REGENTS OF THE UNIVERSITY OF COLORADO, A BODY CORPORATE, Denver, CO (US)

(72) Inventors: Malik Y. Kahook, Denver, CO (US); Naresh Mandava, Denver, CO (US)

(73) Assignee: The Regents of the University of Colorado, A Body Corporate, Denver, CO (US)

( * ) Notice: Subject to any disclaimer, the term of this patent is extended or adjusted under 35 U.S.C. 154(b) by 200 days.

(21) Appl. No.: 15/321,560

(22) PCT Filed: Jun. 11, 2015

(86) PCT No.: PCT/US2015/035331
§ 371 (c)(1),
(2) Date: Dec. 22, 2016

(87) PCT Pub. No.: WO2015/199996
PCT Pub. Date: Dec. 30, 2015

(65) Prior Publication Data
US 2017/0265851 A1    Sep. 21, 2017

Related U.S. Application Data

(60) Provisional application No. 62/017,677, filed on Jun. 26, 2014.

(51) Int. Cl.
*A61B 17/02* (2006.01)
*A61B 3/00* (2006.01)
*A61F 9/00* (2006.01)

(52) U.S. Cl.
CPC ............ *A61B 17/0231* (2013.01); *A61B 3/00* (2013.01); *A61F 2009/0035* (2013.01)

(58) Field of Classification Search
CPC .................................................. A61B 17/0231
(Continued)

(56) References Cited

U.S. PATENT DOCUMENTS 5,267,553 A * 12/1993 Graether ............ A61B 17/0231
600/236
5,318,011 A *  6/1994 Federman ............. B29C 53/086
600/236
(Continued)

FOREIGN PATENT DOCUMENTS

JP       2014193241 A  * 10/2014  ......... A61B 17/0293
JP       2014193248 A  * 10/2014  ......... A61B 17/0231
WO   WO/2013/070423      5/2013

OTHER PUBLICATIONS

International Preliminary Report on Patentability, dated Nov. 30, 2015.
(Continued)

*Primary Examiner* — Eric S Gibson
(74) *Attorney, Agent, or Firm* — Medlen & Carroll, LLP

(57) ABSTRACT

The present disclosure relates to a structure used in an ophthalmic surgical procedure. The device may be used in pupil expansion or stabilization of the iris. The device is made out of an elastic or semielastic material in a shape that is conducive to easy insertion and removal as well as being optimized for atraumatic pupil expansion.

15 Claims, 23 Drawing Sheets

(58) Field of Classification Search
USPC .................................................. 600/236
See application file for complete search history.

(56) References Cited

U.S. PATENT DOCUMENTS

| | | | | |
|---|---|---|---|---|
| 5,334,217 | A * | 8/1994 | Das | A61B 17/0057 606/151 |
| 6,200,336 | B1 * | 3/2001 | Pavcnik | A61F 2/07 623/1.13 |
| 6,620,098 | B1 * | 9/2003 | Milverton | A61B 17/0231 600/208 |
| 8,323,296 | B2 * | 12/2012 | Malyugin | A61B 17/0231 606/107 |
| 8,439,833 | B2 * | 5/2013 | Christensen | A61B 17/0231 600/236 |
| 8,496,583 | B1 | 7/2013 | Reynard | 29/828 |
| 8,852,091 | B2 * | 10/2014 | Sussman | A61B 17/0231 600/208 |
| 8,900,136 | B2 * | 12/2014 | Cote | A61F 9/00736 600/208 |
| D735,857 | S * | 8/2015 | Dykes | D24/150 |
| 9,504,459 | B1 * | 11/2016 | Nallakrishnan | A61B 17/0231 |
| 9,763,653 | B2 * | 9/2017 | Malyugin | A61B 1/32 |
| 9,918,710 | B2 * | 3/2018 | Malyugin | A61B 1/32 |
| 9,974,688 | B2 * | 5/2018 | Malyugin | A61B 17/0231 |
| 9,980,852 | B2 * | 5/2018 | Malyugin | A61B 17/0231 |
| 10,080,558 | B2 * | 9/2018 | Bhattacharjee | A61B 17/0293 |
| 10,098,624 | B2 * | 10/2018 | Nallakrishnan | A61B 17/0231 |
| 2008/0243139 | A1 * | 10/2008 | Dusek | A61B 7/0231 606/107 |
| 2008/0269888 | A1 * | 10/2008 | Malyugin | A61B 17/0231 623/6.42 |
| 2012/0289786 | A1 * | 11/2012 | Dusek | A61B 17/0231 600/236 |
| 2013/0053860 | A1 * | 2/2013 | Malyugin | A61B 17/0231 606/107 |
| 2013/0096386 | A1 * | 4/2013 | Christensen | A61B 17/0231 600/206 |
| 2013/0131458 | A1 * | 5/2013 | Malyugin | A61B 1/32 600/236 |
| 2013/0267988 | A1 * | 10/2013 | Sussman | A61B 17/0231 606/198 |
| 2014/0090653 | A1 | 4/2014 | Clarke | 351/214 |
| 2014/0221759 | A1 * | 8/2014 | Mackool | A61B 17/0231 600/209 |
| 2014/0276900 | A1 * | 9/2014 | Cote | A61F 9/00736 606/107 |
| 2014/0378773 | A1 * | 12/2014 | Dykes | A61B 17/0293 600/208 |
| 2015/0164685 | A1 * | 6/2015 | Bhattacharjee | A61B 17/0231 606/198 |
| 2015/0265269 | A1 * | 9/2015 | Malyugin | A61B 1/32 600/236 |
| 2015/0351736 | A1 * | 12/2015 | Bhattacharjee | A61B 17/0293 600/209 |
| 2015/0366704 | A1 * | 12/2015 | Eippert | A61F 9/007 600/236 |
| 2016/0030239 | A1 * | 2/2016 | Akura | A61B 17/0231 606/107 |
| 2016/0051244 | A1 * | 2/2016 | Akura | A61B 17/0293 600/236 |
| 2016/0081685 | A1 * | 3/2016 | Dykes | A61B 17/0293 606/107 |
| 2017/0265851 | A1 * | 9/2017 | Kahook | A61B 17/0231 |
| 2017/0312126 | A1 * | 11/2017 | Malyugin | A61B 17/0231 |
| 2017/0312127 | A1 * | 11/2017 | Malyugin | A61B 17/0231 |
| 2018/0206835 | A1 * | 7/2018 | Canabrava | A61B 17/00 |

OTHER PUBLICATIONS

Bhattacharjee, S. (2014) "Pupil-expansion ring implantation through a 0.9 mm incision," *Journal of Cataract and Refractive Surgery* 40(7), 1061-1067.

Chang, D. F. (2008) "Use of Malyugin pupil expansion device for intraoperative floppy-iris syndrome: Results in 30 consecutive cases," *Journal of Cataract & Refractive Surgery* 34(5), 835-841.

Rauen, M. et al. (2010) "Partial retraction of Malyugin pupil expansion device to improve safety during ring removal," *Journal of Cataract & Refractive Surgery* 36(3), 522-523.

* cited by examiner

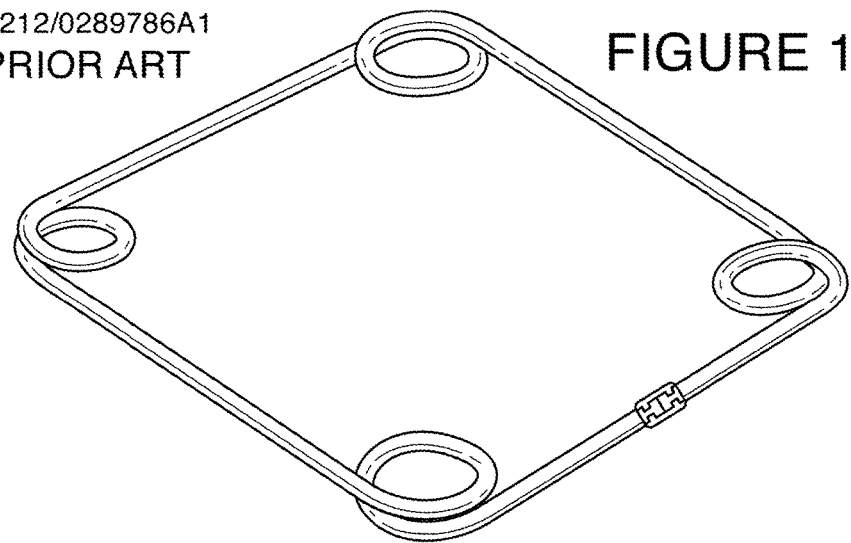
FIGURE 1
FIGURE 2
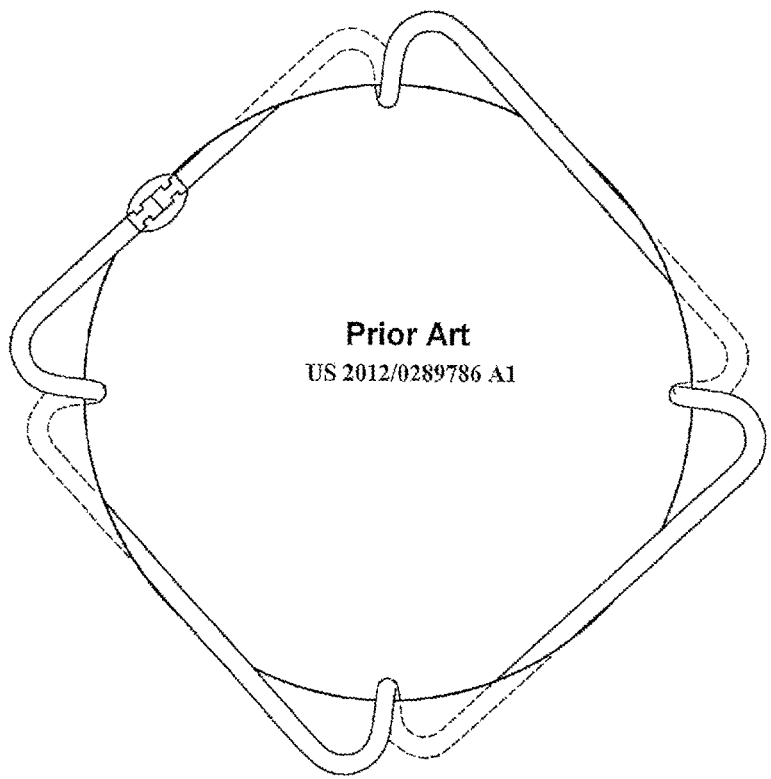

DETAIL B
SCALE 24 : 1

FIGURE 22
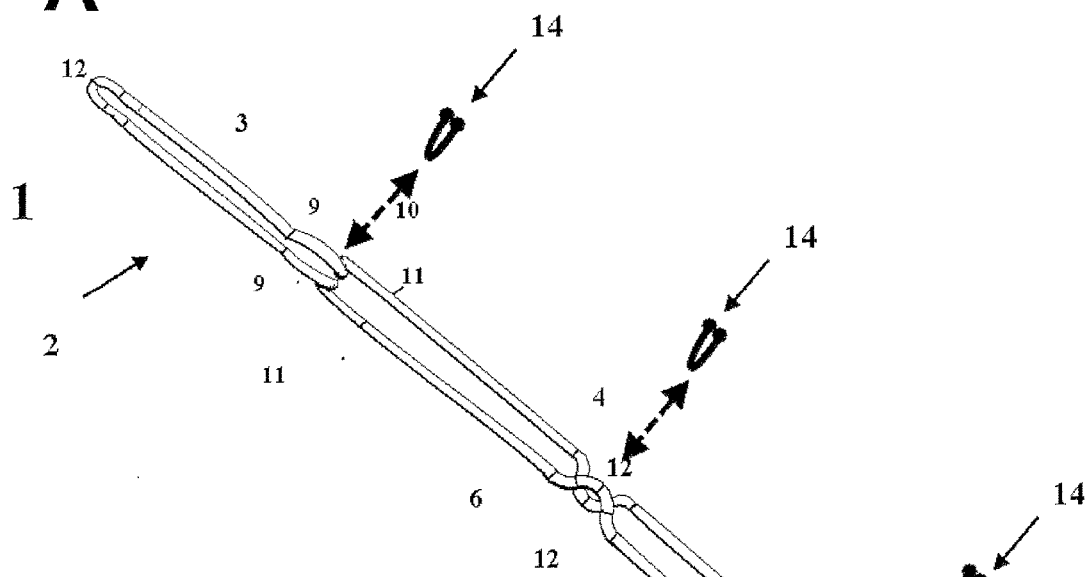
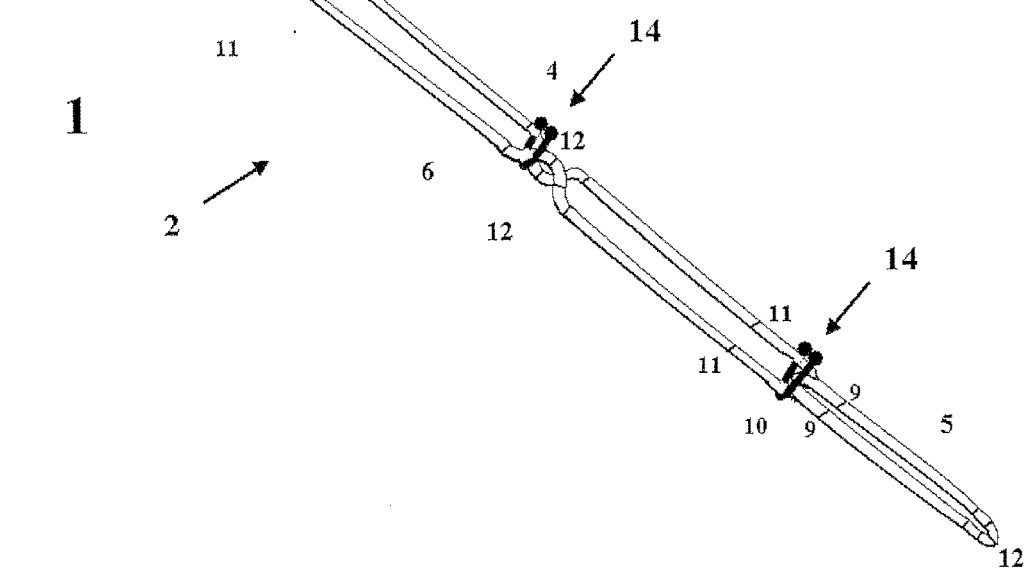

OCULAR TISSUE EXPANSION RING

CROSS-REFERENCE TO RELATED APPLICATIONS

The present application claims the benefit of U.S. Provisional Patent Application No. 62/017,677, filed on. Jun. 26, 2014, which is incorporated herein by reference.

FIELD OF THE INVENTION

The present disclosure relates to a structure used in an ophthalmic surgical procedure. The device may be used in pupil expansion or stabilization of the iris. The device may be made out of an elastic or semi-elastic material in a shape that is conducive to easy insertion and removal as well as being optimized for atraumatic pupil expansion.

BACKGROUND OF THE INVENTION

Intraocular surgery typically requires dilation of the pupil to access posterior tissues from a visual and surgical standpoint. Cataract surgery and retinal surgeries in particular require a well-dilated pupil that allows for visual targeting of tissues posterior to the iris. Many patients do not respond to pupil dilation drops and require the use of various devices to expand the pupil mechanically.

Various ophthalmic procedures require the dilation of the pupil. It is desirable to extend the pupil during the procedure to provide the surgeon with a wide view of the lens. Known techniques for extending and pulling back the iris can cause damage to iris tissue. Patients who have a small pupil pose a major problem and challenge during ophthalmic surgery. When such a patient has cataract or vitreo-retinal surgery and their pupil cannot be easily dilated by mydriatic eye drops, the surgery becomes difficult unless the pupil can be mechanically dilated. Current styles of iris supporting rings tend to snag the incision into the eye as the rings are being removed from the eye after use. This not only make removal more difficult, but it also can lead to the ring scrapping against the endothelial cells lining the inside of the cornea as the surgeon attempts to free the snagged ring. Pharmacological approaches for managing a small pupil during cataract surgery have limitations. A significant problem for the surgeon is decreased visualization, iris trauma due to incarceration into the wound, iris chafing, pupillary margin damage by needles and others. For example, cataractous lenses are typically replaced in a procedure commonly referred to as phacoemulsification. For this procedure, the lens is broken up with an instrument, typically with an ultrasonically driven tool. To perform this procedure safely a surgeon needs to visualize the entire cataracteous lens. There is need for a better technique and device for safely dilating the iris.

During ophthalmic surgery, it is sometimes desirable to enlarge an opening in eyeball tissue, such as, for example, holding the iris open for access through the pupil. It has been proposed that, at least in some cases, expansion be achieved mechanically by one or more devices that engage against opposing edge portions of the eyeball tissue, such as inner edge portions of the iris. Many current devices suffer from significant issues with ease of implantation and with ease of removal once the surgery is over. In addition, the dilation that is produced by most devices results in significant stress on the iris and produces inflammation and atrophy of tissue after surgery. What is needed is a device that is conducive to easy insertion and removal as well as being optimized for atraumatic pupil expansion.

SUMMARY OF THE INVENTION

The present invention relates generally to the field of eye surgery. This invention is in the field of medical devices. The present invention relates to a device constructed from metals, polymers or other materials that are amenable to precise surface modifications and methods for its use, wherein the device assists in pupil expansion. Some embodiments have no moving parts, while other embodiments have features that can be moved, e.g. extended.

In one embodiment, the invention contemplates a pupil-expanding device. In one embodiment, the invention contemplates a device comprising a compressible polygon elastomer loop with an even number of sides having alternating side segments connected by a plurality of non-overlapping involutions, wherein when said involutions are adjacent said involutions alternate in handedness, wherein every other segment is in the same geometrical plane. In one embodiment, said loop comprises at least four segments. In one embodiment, said involutions comprise a continuous curve through three geometric points that are not overlapping with said segments. In one embodiment, at least one segment contains a positional feature. In one embodiment, at least one segment contains at least one positional feature. In one embodiment, said positional feature further comprises an extension that is displaced from the plane of segment containing said positional feature, wherein said feature is higher or lower than the level of the segment in which said positional feature is located. In one embodiment, said positional feature extension is angled 10 degrees in relation to the segment. In one embodiment, said positional feature is a flexible recess. In one embodiment, said positional features are at the midpoint of each segment. In one embodiment, positional features on adjacent segments alternate in being curved inwards toward the center of the device or curved outward away from the center of said device. In one embodiment, said positional feature is a spring loop. In one embodiment, said positional features are indentations in the segments. In one embodiment, each of said segments is straight between said involutions. In one embodiment, each of said segments is linear, but includes a central positional feature that includes a section angled away from the segment culminating in a positional feature between said involutions. In one embodiment, said adjacent segments are at 90-degree angles. In one embodiment, said device further comprises an insertion tube. In one embodiment, said loop may be collapsed and placed into said insertion tube. In one embodiment, said loop may be collapsed wherein the positional features provide flexible points enabling collapse/elongation of the loop. In one embodiment, said loop is stretched/compressed wherein the positional features within a first segment and third segment are pulled in opposite directions, the device collapses, and the second and fourth segments move closer together. In one embodiment, the positional features on the second and fourth segments are essentially touching or overlapping and geometric points on the end of the first segment are adjacent and geometric points on the end of the third segment are adjacent. In one embodiment, said pupil expander further comprises a device stretching/compression tool. In one embodiment, said device stretching/compression tool interfaces with said loop at positional features on opposite sides of said device and elongates the device in a substantially linear, stretched/compressed position. In one embodiment, said loop is made of nitinol or other medical grade metal alloy. In one embodiment, said loop is compressible and after said compression, the loop returns to the loop shape. In one embodiment, said loop is made from a single nitinol wire. In one embodiment, said loop made from a single nitinol wire has side-to-side laser weld that joins the two ends of the nitinol wire to create a closed loop. In one embodiment, said the welded connection in this location minimizes the stress on the connection and prevents an additional, undesired bend point in the loop. In other embodiments, the loop is a single piece. In one embodiment, the loop is made from injection molded single piece. In one embodiment, said elastomer comprises a polymer. In one embodiment, said polymer is selected from the group consisting of: medical grade silicone, hydrophobic acrylic, hydrophilic acrylic, and other common medical grade polymers. In one embodiment, said elastomer further comprises a stiffened polymer backbone with a flexible coating. In one embodiment, loop is flexible. In one embodiment, said loop is made from a polymer. In one embodiment, said polymer is selected from the group consisting of: medical grade silicone, hydrophobic acrylic, hydrophilic acrylic, and other common medical grade polymers. In one embodiment, said loop further comprises a stiffened polymer backbone with a flexible coating. In one embodiment, said loop is coupled with a rigid material. In one embodiment, said rigid material is selected from the group consisting of polypropylene and nitinol. In one embodiment, the loop holds a positive or negative charge. In one embodiment, the loop is made of combined materials of variable durometer values with the lower durometer material in contact with tissue.

In one embodiment, the invention contemplates a linearly stretched/compressed pupil-expanding device comprising a compressible polygon elastomer loop with four sides having alternating side segments connected by a plurality of non-overlapping involutions, wherein when said involutions are adjacent said involutions alternate in handedness, wherein every other segment is in the same geometrical plane, wherein at least one segment contains a positional feature, wherein the positional features within a first segment and third segment are in opposite ends of the linearly stretched/compressed device and the second and fourth segments are adjacent. In one embodiment, said device further comprises a device stretching/compression tool. In one embodiment, said device stretching/compression tool interfaces with said loop at positional features on opposite sides of said device and elongates the device in a substantially linear, stretched/compressed position. In one embodiment, said device stretching/compression tool interfaces with said loop at positional features on opposite sides of said device and compresses the device in a substantially linear, stretched/compressed position.

In one embodiment, the invention contemplates a method of compressing and collapsing a pupil-expanding device as described above. In one embodiment, said pupil expanding device is collapsed by grabbing positional features (opposing loops or outpourings/inpouchings) and twisting one end clockwise or counterclockwise while the other end is stationary twisting in the opposite direction so that the device is collapsed and stretched/compressed.

In one embodiment, the invention contemplates a method of inserting a pupil expanding device into the eye comprising: a) a stretched/compressed pupil expanding device; b) making a cornea or scleral incision such that a connection is made to the anterior chamber of the eye; c) insertion of said device into and through said incision; d) positioning said device in the anterior chamber of the eye; e) manipulating said device into a non-stretched/compressed form; and f) insertion of said device within the pupil and against iris tissue such that it expands the pupil opening. In one embodiment, said stretched/compressed pupil expanding device is the device described above. In one embodiment, manipulating said device into a non-stretched/compressed form comprises removal of a device stretching/compression tool from said device. In one embodiment, said insertion uses an insertion tool to spread opposing segments apart from each other so that the device is elongated and in this process stretched/compressed when the non-engaged sides collapse towards each other as the two engaged parts are spread apart from each other. In one embodiment, said manipulating said device into a non-stretched/compressed form comprises pulling the segments of the device apart. In one embodiment, said insertion of said device against iris tissue at the rim of the pupil so that it expands the pupil opening expanding the linearly stretched/compressed pupil expanding device such that opposite segments are parallel and then placing a first, lower segment underneath the edge of the pupil such that adjacent upper segments articulate above the edge of the pupil, then subsequently manipulate the other lower segment beneath the edge of the pupil. In one embodiment, said insertion of said device into the pupil of the eye such that it expands the opening of the iris comprises expanding the linearly stretched/compressed pupil expanding device such that opposite segments are parallel and then placing a first, lower segment underneath the edge of the pupil such that adjacent upper segments articulate above the edge of the pupil, then subsequently manipulate the other lower segment beneath the edge of the pupil.

In one embodiment, the invention contemplates a method of removing a pupil-expanding device from the eye comprising: a) a pupil-expanding device positioned within the pupil of the eye; b) articulating the segments from underneath the edge of the pupil; and c) drawing said device through a surgical opening out of the eye. In one embodiment, a method of removing a pupil-expanding device from the eye comprises using a removal tool that spreads to opposing segments apart from each other so that the device is elongated and in this process stretched/compressed when the non engaged sides collapse towards each other as the two engaged parts are spread apart from each other. In one embodiment, said removal tool comprises modified surgical pliers. In one embodiment, said pupil expanding device is the device described above.

In one embodiment, the invention contemplates a pupil expander for use in connection with the inner periphery of the iris of a human eye during human eye surgery, comprising; a) a structure for dilating a pupil during an ophthalmic procedure, comprising a ring, the ring being closed upon itself and not having free ends, and having an inner periphery and an outer periphery, four segments, and four corners connecting said segments containing corners formed by said ring curving through three geometric points that are not overlapping with said segments, wherein said segments separated by two corners lie in the same geometrical plane. In one embodiment, the angle of the two segments that form the first point is between 30 and 180 degrees similar to the angle formed at the third point and the bend at the second point is rounded. In one embodiment, said ring is shaped as a rectangle. In one embodiment, said ring is shaped as a square. In one embodiment, said ring includes straight segments between respective corners. In one embodiment, said adjacent segments are at 90-degree angles. In one embodiment, said angle between the first point and second point is between 30 and 180 degrees. In one embodiment, vertical distance between the first point and second points is between 100 and 400 microns. In one embodiment, said angle between the second point and third point is between 30 and 180 degrees. In one embodiment, at least one first segment contains a positional feature. In one embodiment, said positional feature is a flexible recess. In one embodiment, said positional features are at the midpoint of each segment. In one embodiment, positional features on adjacent segments alternate in being curved inwards toward the center of the device or curved outward away from the center of said device. In one embodiment, said segments connected by a shared corner lie in separate geometrical planes. In one embodiment, said pupil expander further comprises an insertion tube. In one embodiment, said ring may be collapsed and placed into said insertion tube. In one embodiment, said ring may be collapsed wherein the positional features provide flexible points enabling collapse/elongation of the ring. In one embodiment, said ring is stretched/compressed wherein the positional features within a first segment and third segment are pulled in opposite directions, the device collapses, and the second and fourth segments move closer together. In one embodiment, the positional features on the second and forth segments are essentially touching or overlapping and geometric points on the end of the first segment are adjacent and geometric points on the end of the third segment are adjacent. In one embodiment, said pupil expander further comprises a device stretching/compression tool. In one embodiment, said device stretching/compression tool interfaces with said ring at positional features on opposite sides of said device and elongates the device in a substantially linear, stretched/compressed position. In one embodiment, said ring is made of nitinol or other medical grade metal alloy. In one embodiment, said ring is made from a single nitinol wire. In one embodiment, said ring is made from a single nitinol wire has side to side laser weld that joins the two ends of the nitinol wire to create a closed loop. In one embodiment, said the welded connection in this location minimizes the stress on the connection and prevents an additional, undesired bend point in the ring. In other embodiments, the ring is a single piece. In one embodiment, the ring is made from injection molded single piece. In one embodiment, said ring is made from a polymer. In one embodiment, said ring is flexible. In one embodiment, said polymer is selected from the group consisting of: medical grade silicone, hydrophobic acrylic, hydrophilic acrylic, and other common medical grade polymers. In one embodiment, said ring is compressible and after said compression the ring returns to the ring shape. In one embodiment, said ring further comprises a stiffened polymer backbone with a flexible coating.

In one embodiment, the invention contemplates a structure for dilating a pupil during an ophthalmic procedure, comprising a ring, the ring being closed upon itself and not having free ends, and having an inner periphery and an outer periphery, four segments, and four corners connecting said segments containing corners formed by said ring curving through three geometric points that are not overlapping with said segments, wherein said segments engage the perimeter of the iris, wherein the first and third segments articulate underneath said iris and second and fourth segments articulate on the top of said iris, In one embodiment, the device in a substantially linear position during insertion into the eye before placement into the pupil. In one embodiment, said ring includes straight segments between respective corners. In one embodiment, the iris is inserted on top of a first geometric point and below a third geometric point and against said second geometric point and is held in place by the tension the entire ring produces against the iris tissue when in place. In one embodiment, the angle of the two segments that form the third geometric point is between 30 and 180 degrees similar to the angle formed at said first geometric point and the bend at the second geometric point is rounded to atraumatically receive the iris. In one embodiment, the vertical distance between the first point and second points is between 100 and 400 microns. In one embodiment, said structure further comprises an insertion tube. In one embodiment, said ring may be collapsed and placed into said insertion tube.

It is not intended that embodiments of the invention be limited to any particular method or device confirmation; however, it is believed that the device may be optimally designed to pupil expansion.

DEFINITIONS

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As used herein, the terms "prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

As used herein, the terms "medication" or "therapeutic agent" refer to something that treats or prevents or alleviates the symptoms of a disease or condition, a drug or pharmaceutical composition. Medication is considered to be delivered or present in therapeutically effective amounts or pharmaceutically effective amounts.

As used herein, the terms "medical device," "implant," "device," "medical device," "medical implant," "implant/device," and the like are used synonymously to refer to any object that is designed to be placed partially or wholly within a patient's body (whether permanently or temporarily) for one or more therapeutic or prophylactic purposes such as for tissue augmentation, contouring, restoring physiological function, repairing or restoring tissues damaged by disease or trauma, and/or delivering therapeutic agents to normal, damaged or diseased organs and tissues. While medical devices are normally composed of biologically compatible synthetic materials (e.g., medical-grade stainless steel, titanium and other metals; exogenous polymers, such as polyurethane, silicon, PLA, PLGA, PGA, PCL), other materials may also be used in the construction of the medical implant.

As used herein, the term "elastomer" refers to generally to a polymer or alloy with viscoelasticity (having both viscosity and elasticity) and very weak inter-molecular forces, generally having low Young's modulus and high failure strain compared with other materials.

As used herein, the term "ring" refers to generally to a substantially circular shape (e.g. a circle, oval, loop, or ellipse), but not necessarily one without small gaps or openings. A ring as described herein need not be a completely closed loop. Indeed, embodiments are shown in the figures where there is a small opening in the circle or ring.

As used herein, the term "involution" refers to generally to a structural feature found on the device which is the curve section formed as the loop travels through three geometric points transitioning from one segment to the next. The curve involution of the involution has a handedness, either left or right handed in nature. In most embodiments, the involution is a transition from an upper segment to a lower segment or vice versa.

As used herein, the term "corner" refers to generally to a structural feature found on the device where one segment intersects with another segment. In most cases, the corners are not pointed outwards, but point inwards and are comprised of involutions.

As used herein, the term "positional feature" refers to generally to a structural feature found on the device, which enables the device to be adjusted positionally and also may provide a flexible position from which the ring/loop may be bent to allow collapsing of the ring/loop. Such features enable the device to be substantially collapsed and subsequently placed into an insertion tube. Positional features may be loops, spring loops, recesses, indentations, or other features that enable greater flexibility, but are substantially rigid when the ring/loop is not in a collapsed state. Positional features that are recesses, indentations, or arcs may be positioned generally inward or outward and are usually within the geometrical plane of the segment in which they are found. In most embodiments, the positional features are found within the segments of the device.

As used herein, the terms "superior" and "posterior" refer to the portion furthest from, and closest to, the patient, respectively.

As used herein, the term "implanted" refers to having completely or partially placed a device within a host. A device is partially implanted when some of the device reaches, or extends to the outside of a host.

The present invention contemplates devices configured to be compatible with engaging the iris. As used herein, the term "compatible" refers to an articulation of elements that conforms closely to anatomical features and device features or surfaces. For example, in one embodiment, the present invention contemplates a device configured and dimensioned such that it can be inserted into the anterior chamber of the eye through a previously prepared scleral incision and be drawn into an insertion tube and, after insertion of the tube into the anterior chamber of the eye manipulated to expand the opening of the iris for subsequent surgery. Thus the device is also flexible and compactable to be placed into an insertion tube. The method of use of this pupil expander comprises the moving of the pupil expander, which is inserted into the anterior chamber of the eye through a previously prepared scleral incision. The device can be drawn into an insertion tube and, after insertion of the tube into the anterior chamber of the eye, such as through a small slit in the cornea, projected from the tube and manipulated to expand the opening of the iris.

As used herein, the term "device stretching/compression tool" refers to a companion device used in conjunction with the ring/loop device of the current invention to hold the ring/loop in a stretched/compressed conformation. In most embodiments, such stretched/compressed confirmation is a linear compression of the ring/loop device, such as shown in FIGS. 21A&B. In some embodiments, the device stretching/compression tool is substantially linear with two ends having receiving features upon which the ring/loop device articulates. In one embodiment, the ring/loop may be articulated onto said device stretching/compression tool 14 by positioning the positional feature positional features 12 within segments 3 and 5 and the device stretching/compression tool 14 and said positional features 12 are pulled in opposite directions and the device collapses and segments 4 and 6 move closer together. FIG. 20B shows wherein the positional features 12 on segments 4 and 6 are essentially touching or overlapping and geometric points 10 on the end of segment 3 are adjacent and geometric points 10 on the end of segment 5 are adjacent. In one embodiment, said device stretching/compression tool 14 interfaces with said loop at positional features on opposite sides of said device and elongates the device in a substantially linear, stretched/compressed position. In one embodiment, said device stretching/compression tool interfaces with said loop at positional features on opposite sides of said device and compresses the device inward into a substantially linear, stretched/compressed position, such as shown in FIGS. 22A&B. In one embodiment, said device stretching/compression tool is several clips, which articulate around the stretched/compressed device, such as shown in FIGS. 23A&B. In FIGS. 23A&B, the clips attached to the backbone articulate around the stretched/compressed device and keep the stretched/compressed device in a substantially linear position during insertion into the eye.

As used herein, the term "insertion tool" refers to a companion device used to enable deployment of the stretched/compressed version of the pupil-expanding device into the desired position within the pupil of the eye. In one embodiment, the insertion tool is used spread opposing segments of the pupil-expanding device apart from each other so that the device is elongated and in this process stretched/compressed when the non-engaged sides collapse towards each other as the two engaged parts are spread apart from each other. In one embodiment, the insertion tool interfaces with the positional features on the stretched/compressed version of the pupil-expanding device. In one embodiment, said insertion tool are modified surgical pliers.

As used herein, the term "removal tool" refers to a companion device used in removing the device of the current invention from the eye, particularly when the pupil-expanding device is in place in the eye. In one embodiment, the removal tool is used to spread opposing segments apart from each other so that the device is elongated and in this process stretched/compressed when the non-engaged sides collapse towards each other as the two engaged parts are spread apart from each other. In some embodiments, the removal tool may be used to load the device back upon the device stretching/compression tool to enable removal from the eye.

As used herein, the term "nitinol" refers to a metal alloy of nickel and titanium, where the two elements are present in roughly equal atomic percentages. Nitinol alloys exhibit two closely related and unique properties: shape memory and superelasticity (also called pseudoelasticity). Shape memory refers to the ability of nitinol to undergo deformation at one temperature, and then recover its original, undeformed shape upon heating above its "transformation temperature". Superelasticity occurs at a narrow temperature range just above its transformation temperature; in this case, no heating is necessary to cause the undeformed shape to recover, and the material exhibits enormous elasticity, some 10-30 times that of ordinary metal.

Any concentration range, percentage range, or ratio range recited herein are to be understood to include concentrations, percentages or ratios of any integer within that range and fractions thereof, such as one tenth and one hundredth of an integer, unless otherwise indicated. In addition, any number range recited herein relating to any physical feature, such as polymer subunits, size or thickness, are to be understood to include any integer within the recited range, unless otherwise indicated. It should be understood that the terms "a" and "an" as used above and elsewhere herein refer to "one or more" of the enumerated components. For example, "a" polymer refers to either one polymer or a mixture comprising two or more polymers. As used herein, the term "about" means±15%.

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 1 shows a prior art expansion ring for eyeball tissue.

FIG. 2 shows another prior art expansion ring for eyeball tissue.

FIG. 13 also shows an example of a loop positional feature 12.

FIGS. 17 A&B show a manufactured embodiment of the device made from a single nitinol wire.

FIG. 20A shows an initial phase of compression of the device wherein the positional features 12 within segments 3 and 5 are pulled in opposite directions and the device collapses and segments 4 and 6 move closer together. FIG. 20B shows wherein the positional features 12 on segments 4 and 6 are essentially touching or overlapping and geometric points 10 on the end of segment 3 are adjacent and geometric points 10 on the end of segment 5 are adjacent.

FIG. 21A shows a stretched/compressed embodiment of the current invention with the device stretching/compression tool next to the linearly stretched/compressed ring/loop 2 with arrows indicating how it will articulate with the linearly stretched/compressed ring/loop 2.

FIGS. 22A&B show the stretched/compressed version of one embodiment of the pupil expander, which further comprises a device stretching/compression tool 14. In one embodiment, said device stretching/compression tool interfaces with said loop at positional features on opposite sides of said device and compresses the device inward into a substantially linear, stretched/compressed position. In one embodiment, said device stretching/compression tool has several clips that articulate around the stretched/compressed device.

Figure 3:
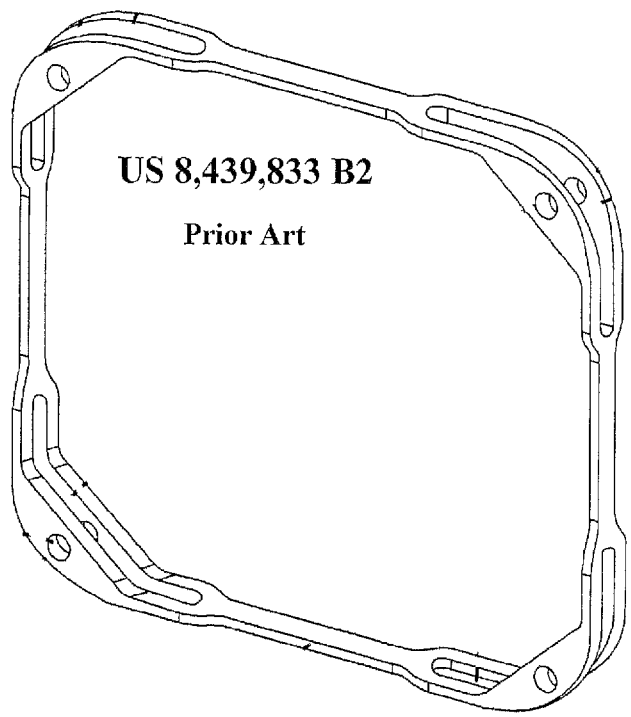
FIG. 3 shows a square prior art ophthalmic structure for dilating a pupil during an ophthalmic procedure.

LIST OF REFERENCE NUMERALS 1 the device
2 loop/ring
3 first segment
4 second segment
5 third segment
6 fourth segment
7 involution
8 corner
9 first geometric point
10 second geometric point
11 third geometric point
12 positional feature 13 insertion tube
14 device stretching/compression tool
15 insertion tool
16 removal tool

DESCRIPTION OF THE INVENTION

The present disclosure relates to a structure used in an ophthalmic surgical procedure. The device may be used in pupil expansion or stabilization of the iris. The device made out of an elastic or semielastic material in a shape that is conducive to easy insertion and removal as well as being optimized for atraumatic pupil expansion.

Other devices are known in the field of ophthalmic surgery, in particular for pupil expansion or iris stabilization. One particular design is described in U.S. patent application Ser. No. 13/291,946 [1]. This application describes an extension device for eyeball tissue comprising a strand of resilient material having multiple tissue-engaging portions for engaging and spreading eyeball tissue segments apart, said strand being formed as a continuous ring with straight sides joined by corner portions, said corner portions constituting the tissue-engaging portions and having top and bottom sections and a connecting arc of the strand to form gap for receiving the tissue (See FIG. 1). This device has been marketed as the Malyugin ring. The application claims a version in which the top and bottom sections do not overlap. A version of this is shown in FIG. 2, "the dimensions of the ring and the various bends are chosen so that minimal abrasive force is applied to the iris, and no or essentially no pinching or clamping force. Dimensions are selected such that the opening formed by each return bend 82 is at least as great as the marginal thickness of the iris, with no coils or loops located one above the other." The reference does not teach a device having parallel opposite segments or opposing segments in the same plane, but rather shows angled segments and requires corner coils of similar handedness. The use of the Malyugin device is further described by Chang, D. F. (2008) *J. Cataract. Refract. Surg.* 34(5), 835-841 [2]. This reference describes a report of 30 uses of the Malyugin device described above. This report specifically describes the successful use of the device in cases of floppy-iris syndrome. The reference describes the Malyugin device as far superior to other mechanical pupil expansion devices. The images within this reference demonstrate the iris engagement described in the application Ser. No. 13/291,946 [1]. The reference does not teach a device having parallel opposite segments or opposing segments in the same plane, but rather shows angled segments and requires corner coils of similar handedness. Another reference, Rauen, M. and Oetting, T. (2010) *J. Cataract. Refract. Surg.* 36(3), 522-523 [3], describes intraoperative behaviors of the Malyugin device above that can limit safe usage. For example, complete retrieval of the ring into the inserter barrel during ring removal can result in unpredictable and chaotic ring behavior that can damage intraocular structures. The reference further describes a method of partial retraction to limit potential damage by the Malyugin device. The reference does not teach a device having parallel opposite segments or opposing segments in the same plane, but rather shows angled segments and requires corner coils of similar handedness.

The difficulty with the Malyugin device is that the rings are difficult to engage with the iris and removal can be difficult due to the loops hooking onto the inserter and removal device. The loops of the Malyugin device disengage from the iris during surgeries and are difficult to reposition. Another major issue is that the loops of the Malyugin device overlap each other when engaged to the iris, so the upper and lower portions of the double loop rub against the iris and produce inflammation and atrophy of tissue. It would be desirable to have a device, like the present invention, to engage the iris without overlapping above and below the iris so that atrophy and manipulation is minimized. It is important to explain that the present invention may use insertion and removal tools that can act by either compressing two sides of the ring/loop against each other or pushing to opposite sides away from each other. This is different from what Malyugin does, for example where the Malyugin device is hooked and pulled into a lumen.

In contrast with the Malyugin device, the device of the present invention: 1) Does not have loops that engage the iris; 2) Does not have an engaging portion that overlaps above and below the iris; 3) May have features at least 8 different locations that lead to collapse of the device when inserting and removing (Malyugin only has four); and the present invention may have positioning features (see "12" in FIG. 11, FIG. 13, and FIG. 19) which are independent from the features that engage the iris. These features are unlike the Malyugin, which uses the actual iris capturing features to also act as positioning holes within the eyes, using the same holes to both engage iris as well as use for positioning may lead to injury to the iris when the holes are engaged and iris tissue is present within the rings.

Figure 4:
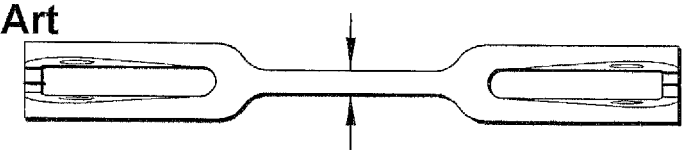
FIG. 4 shows a side view of a square prior art ophthalmic structure for dilating a pupil during an ophthalmic procedure.

Another device is described in U.S. Pat. No. 8,439,833 [4]. This reference describes a ring for dilating a pupil during an ophthalmic procedure includes a series of spaced supports for engaging an iris perimeter, shown in FIG. 3. The supports are plate elements that form an open pocket directed outwardly for engaging the iris. The sides of the ring form a primary plane, and the plates are located in respective planes above and below the primary plane as shown in FIG. 4. The outer periphery of the top and bottom plates forms a lip feature that is the opening to the pocket, which retains the iris. This continuous ring also contains a recess on each corner that engages the iris above and below the iris. They describe "pockets" that engage the iris. This device has four pockets. These pockets are rigid and make folding into an inserter and extractor difficult. This device does not describe an engagement device that articulates alternatively over and under the iris tissue with articulation at the involutions as described in the present invention. In addition, the anatomy of the anatomic iris plane can be variable and the restrictive nature of the form of the device can make it difficult for positioning as well as for atraumatic removal.

Figure 5:
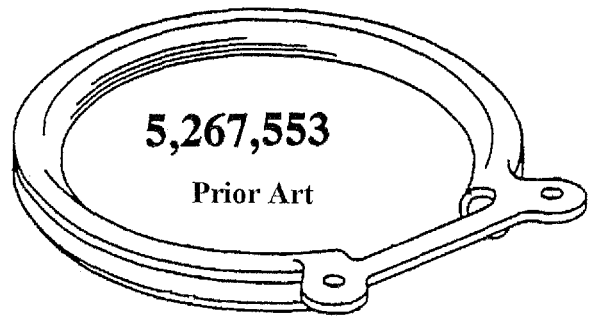
FIG. 5 shows a prior art circular iris expander device.

Another device is described in U.S. Pat. No. 5,267,553 [5]. This patent describes a method of creating an iris expander by pressing out a grooved material into a circular shape. The groove engages the iris tissue. The pupil expander has an elongated plastic resilient hollow ring that is C-shaped in cross section, and formed into a partial circle, shown in FIG. 5. The ends of the ring member have perforated tabs thereon, and are connected together by a strap. The pupil expander is stretched/compressed into an elongated shape. Forceps tips are inserted into the ends of the ring member to hold the ring member during insertion of the expander into the anterior chamber of the eye through an incision in the eye outside the location of the iris. The device is designed to articulate with the iris on the inner groove of the device rather than over and under the edge of a continuous loop. It has a continuous recess that engages the iris in a "C" configuration (with a bar to close to the "C") but slippage is a major issue and it also this continuous recess results in overlapping of the iris above and below which has similar issues as the Malyugin device.

Figure 6:
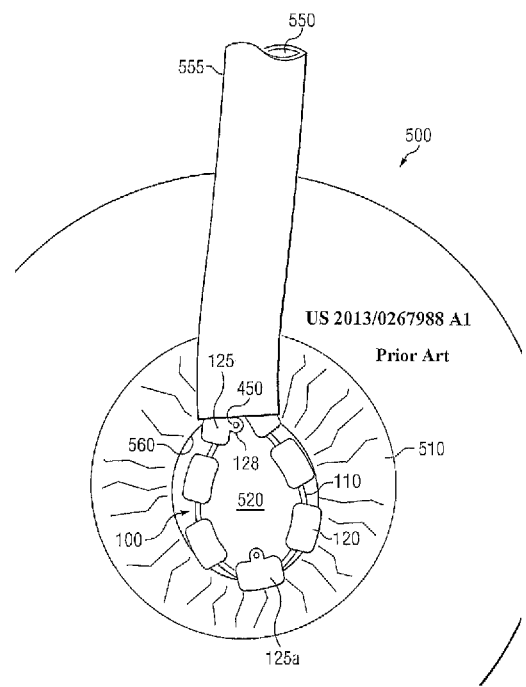
FIG. 6 shows a prior art device that has iris engaging segments connected by a central element.

Another device is described in U.S. patent application Ser. No. 13/438,881 [6]. This application describes a device that has iris-engaging segments connected by a central element. The pupil expander comprises a support member and a plurality of engaging portions. The support member is sized to expand a pupil. The engaging portions are coupled to and spaced about the support member. The engaging portions each have a recess shaped and sized to receive an inner margin of an iris. The device is shown being deployed in FIG. 6. The supporting members engage the iris of the eye through a groove rather than the than over and under the edge of a continuous loop Another device is described in U.S. Pat. No. 8,496,583 [7]. This patent describes a pupil dilation system for dilating a pupil of an eye by application of a substantially uniform expansile force around the circumference of the pupil, while precluding focal stress points that may damage the iris. The pupil dilation system describes the pupil dilator and a cannular injection device. The device is designed to articulate with the iris on the inner groove of the device rather than over and under the edge of a continuous loop.

Another device is Morcher Pupil Dilator described at world wide web.fci-ophthalmics.com/cataract#morcher_pupil. The Morcher pupil dilator type 5S is described as a semi-circular elastic PMMA ring for the expansion of the pupil during phacoemulsification. The website states that this serves as a temporary implant for patients who have cataracts and contracted pupils or floppy iris syndrome. The supporting members engage the iris of the eye through a groove rather than the over and under the edge of a continuous loop. These are really a different class of pupil expansion devices. Iris hooks are inserted partially through small incisions to "hook" the iris. Multiple incisions are required. These manual devices simply stretch the iris but do not hold it in place after stretching (there is no implant).

Another device is Milvella "PerfectPupil® Injectable" flexible iris expansion ring. This reference describes another device, which forms an injectable plastic central groove with iris engagement tabs and positional holes. The supporting members engage the iris of the eye through a groove rather than the over and under the edge of a continuous loop. This is not a continuous ring and has many "pockets" for engaging the iris. This device carries the same insertion and removal issues as the other devices.

Figure 7:
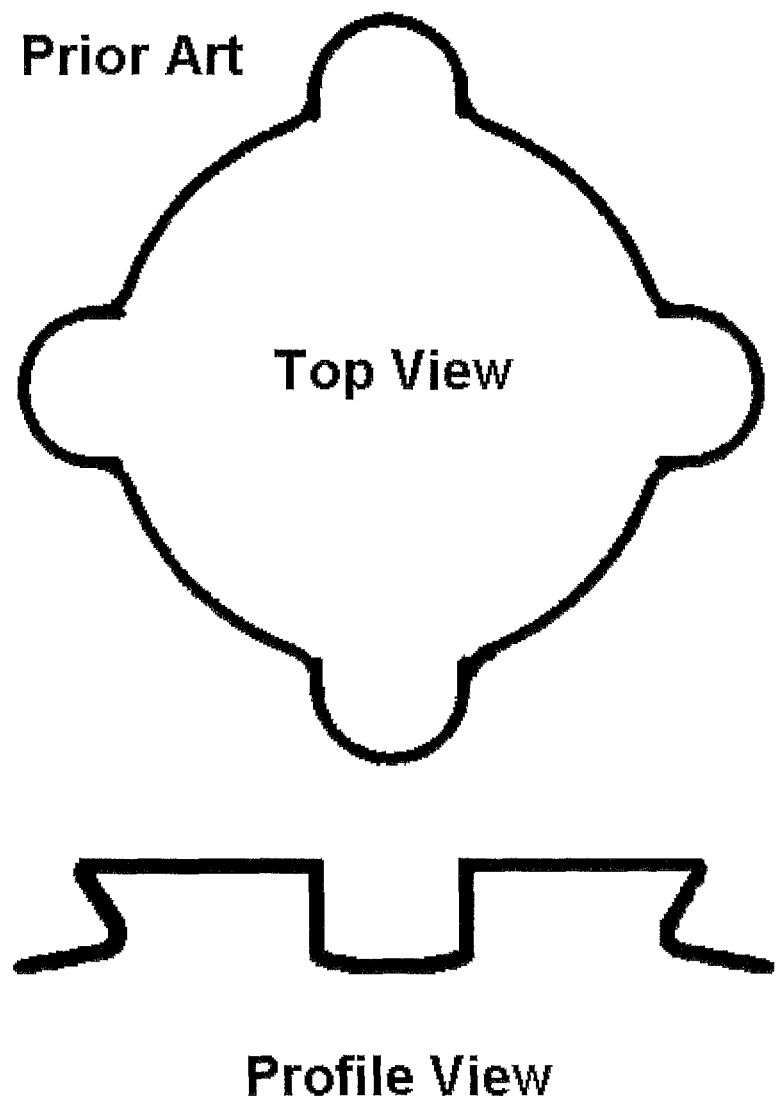
FIG. 7 shows a top and side view of a prior art device, the Xpand iris speculum.

Another device is the diamatrix XPand iris expansion system. The Xpand device, shown in FIG. 7, is composed of four horizontal portions that are on the same plane along with four iris engaging features (referred to as "feet" by the manufacturer) that curve under the plane of the horizontal portions to engage the iris within recesses that engage the iris anteriorly and posteriorly. The four beams that are horizontal and on the same plane would ride over the iris post insertion as opposed to the current invention which has two beams (segments) above and two beams (segments) below the iris when engaged. The configuration of the Xpand device leads to significant chafing, stress on the ocular tissue, and has problems with stability in addition to difficulty of insertion and removal of the device. The configuration of the current invention allows for greater and more secure engagement of the iris. In addition, there are no positioning holes/features on the Xpand device and the device is disengaged from the iris by maneuvering the iris engaging portions away from the iris, which would potentially cause damage to the iris if there iris were to be pinched or disrupted while moving the ring. The lack of engaging features on the Xpand also limits options for insertion and removal of the device.

Figure 8:
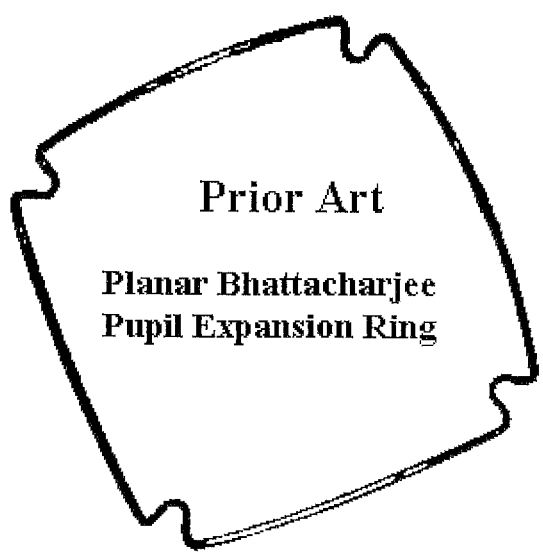
FIG. 8 shows a prior art device, the planar Bhattacharjee Pupil Expansion Ring. This ring/loop of this device lies all in one geometric plane. When engaging this device in the pupil, the pupil must be stretched with the iris tucked under one flange and over the next flange of the device, creating significant stress on the device as well as mechanical pressure on the iris tissue since the device must be deformed to perform effectively. This also may require two instruments including one acting to stabilize the ring and a second to tuck the flange appropriately. This also may cause increased iris chaffing and mechanical damage during removal of the device.

Another device is the planar Bhattacharjee Pupil Expansion Ring, described in Bhattacharjee (2014) [8], shown in FIG. 8. This ring/loop of this device lies all in one geometric plane. When engaging this device in the pupil, the pupil must be stretched with the iris tucked under one flange and over the next flange of the device, creating significant stress on the device as well as mechanical pressure on the iris tissue since the uniplanar device must be deformed to perform effectively. This also may require two instruments including one acting to stabilize the ring and a second to tuck the flange appropriately. This also may cause increased iris chaffing and mechanical damage during removal of the device.

Current Invention

Intraocular surgery typically requires dilation of the pupil to access posterior tissues from a visual and surgical standpoint. Cataract surgery and retinal surgeries in particular require a well-dilated pupil that allows for visual targeting of tissues posterior to the iris. Unfortunately, many patients do not respond to pupil dilation drops and require the use of various devices to expand the pupil mechanically. Each of the prior art devices previously described have significant issues with ease of implantation and with ease of removal once the surgery is over. In addition, the dilation that is produced by most is created by overlapping of the iris or other configurations, which result in significant stress on the iris, and produces inflammation and atrophy of tissue after surgery. In one embodiment, the current device is made out of an elastic or semielastic material in a shape that is conducive to easy insertion and removal as well as being optimized for atraumatic pupil expansion compared to all other devices on the market.

In one embodiment, the invention contemplates a device comprising a compressible polygon elastomer loop with an even number of sides having alternating side segments connected by a plurality of non-overlapping involutions, wherein when said involutions are adjacent said involutions alternate in handedness, wherein every other segment is in the same geometrical plane. In one embodiment, said loop comprises at least four segments. In one embodiment, said involution comprises a continuous curve through three geometric points that are not overlapping with said segments. In one embodiment, at least one segment contains a positional loop. In one embodiment, said positional features are spring loops. In one embodiment, each of said segments is straight between said involutions. In one embodiment, each of said segments contain a slightly out of plane angled positional feature between said involutions. In one embodiment, said adjacent segments are at 90-degree angles. In one embodiment, said loop is made of nitinol or other medical grade metal alloy. In one embodiment, said loop is compressible and after said compression the loop returns to the loop shape. In one embodiment, said elastomer comprises a polymer. In one embodiment, said polymer is selected from the group consisting of: medical grade silicone, hydrophobic acrylic, hydrophilic acrylic, and other common medical grade polymers. In one embodiment, said elastomer further comprises a stiffened polymer backbone with a flexible coating. In one embodiment, loop is flexible. In one embodiment, said loop is made from a polymer. In one embodiment, said polymer is selected from the group consisting of: medical grade silicone, hydrophobic acrylic, hydrophilic acrylic, and other common medical grade polymers. In one embodiment, said loop further comprises a stiffened polymer backbone with a flexible coating. In one embodiment, said loop is coupled with a rigid material. In one embodiment, said rigid material is selected from the group consisting of polypropylene and nitinol. In one embodiment, the loop holds a positive or negative charge. In one embodiment, the loop is made of combined materials of variable durometer values with the lower durometer material in contact with tissue.

In one embodiment, the invention contemplates a pupil expander for use in connection with the inner periphery of the iris of a human eye during human eye surgery, comprising; a) a structure for dilating a pupil during an ophthalmic procedure, comprising a ring, the ring being closed upon itself and not having free ends, and having an inner periphery and an outer periphery, four segments, and four corners connecting said segments containing corners formed by said ring curving through three geometric points that are not overlapping with said segments, wherein said segments separated by two corners lie in the same geometrical plane. In one embodiment, the angle of the two segments that form the first point is between 30 and 180 degrees similar to the angle formed at the third point and the bend at the second point is rounded. In one embodiment, said ring is shaped as a rectangle. In one embodiment, said ring is shaped as a square. In one embodiment, said ring includes straight segments between respective corners. In one embodiment, said adjacent segments are at 90-degree angles relative to each other. In one embodiment, said angle between the first point and second point is between 30 and 180 degrees. In one embodiment, vertical distance between the first point and second points is between 100 and 400 microns. In one embodiment, said angle between the second point and third point is between and 30 and 180 degrees. In one embodiment, at least one segment contains a loop. In one embodiment, said segments connected by a shared corner lie in separate geometrical planes. In one embodiment, said loop is made of nitinol or other medical grade metal alloy. In one embodiment, said ring is made from a polymer. In one embodiment, said ring is flexible. In one embodiment, said polymer is selected from the group consisting of: medical grade silicone, hydrophobic acrylic, hydrophilic acrylic, and other common medical grade polymers. In one embodiment, said ring is compressible and after said compression the ring returns to the ring shape. In one embodiment, said ring further comprises a stiffened polymer backbone with a flexible coating.

The present invention, in a preferred embodiment having four segments, four involutions, and four positional features has significant advantages over previous devices designed for pupil extension. 1) The spring type positional features in conjunction with the iris engaging involutions provide 8 points for compressibility of the current device, which allows for greater flexibility with positioning. 2) Spring loops allow for positioning of the device to expand the iris without needing to manipulate the areas that actually engage iris . . . this allows for safer implantation. 3) The design of the present device allows for a low profile (400 microns high) as opposed to the diamatrix device for example which is 1.2 mm high due to their use of four speculum like projections that engage iris which need to come off the main body of the device. In the current device, the four involutions, which form "corners", are continuous with the four main beams/segments that compose the majority of the ring body. 4) The methods for implantation of the current device compared to the others has distinct advantages. The method of inserting and removing the present device that leverages the spring loops is different and has advantages over previous methods and other devices. Due to the flexibility of the device of current invention, the device may be collapsed easily and in some embodiments placed, for instance in an insertion tube 13 while it is delivered through an incision to the appropriate position within the eye. Once delivered, the ring/loop 2 may be removed from the insertion tube 13 (or if there is no insertion tube, the device is expanded) and positioned within the iris. Positional adjustments are further made using the positional features 12, recesses or loops, within the segments ((3, 4, 5, and 6). In one embodiment, said pupil expander further comprises a device stretching/compression tool 14. In one embodiment, said device stretching/compression tool 14 interfaces with said loop at positional features on opposite sides of said device and elongates the device in a substantially linear, stretched/compressed position.

Figure 9:
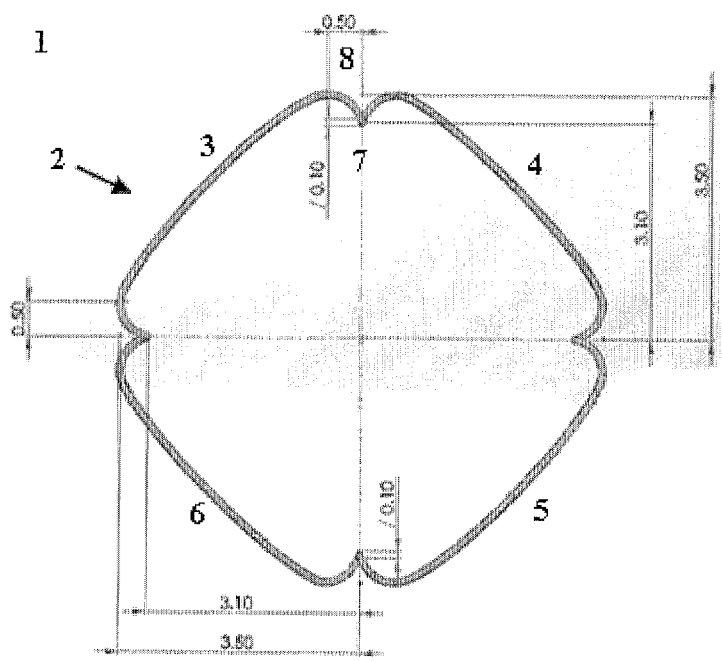
FIG. 9 shows one embodiment of the current device 1 with four segments (3, 4, 5, and 6). The segments are connected by involutions 7 of the device loop/ring 2. The involutions are formed as the loop travels through three geometric points. The transition of segment to segment through each involution comprises a corner 8 of the device. The handedness of the curved involution 7 alternates at subsequent involutions. Practically this means that the handedness of each involution 7 will alternate from a right-handed curve to left-handed curve at the next involution 7. Measurements are in millimeters.

FIG. 9 shows one embodiment of the current device 1 with four segments (3, 4, 5, and 6). The segments are connected by involutions 7 of the device loop/ring 2. The involutions are formed as the loop travels through three geometric points. The transition of segment to segment through each involution comprises a corner 8 of the device. The handedness of the curved involution 7 alternates at subsequent involutions. Practically, this means that the handedness of each involution 7 will alternate from a right-handed curve to left-handed curve at the next involution 7. Measurements are in millimeters.

Figure 10:
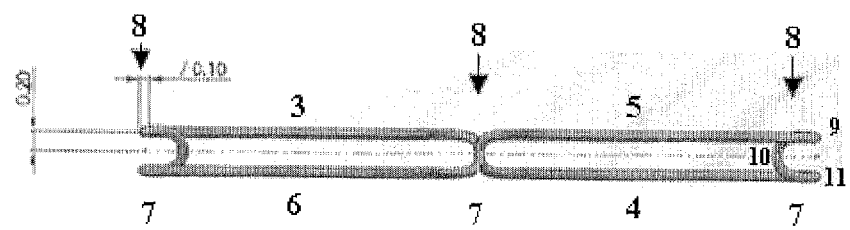
FIG. 10 shows a side view of the current device 1 with four segments (3, 4, 5, and 6) with a view from the side of the device with the third segment 5 and fourth segment 6 closest to the viewer and the corner 8 between these segments in the center. The three geometric points comprising the involution 7 between the second segment 4 and third segment 5 are shown in the right hand portion of the figure. The involution 7 proceeds from the third segment 5 via the first geometric point 9 through the second geometric point 10 to the third geometric point 11. This particular involution 7, between the second segment 4 and third segment 5, is a left-handed curve. The three geometric points are non-overlapping.

FIG. 10 shows a side view of the current device 1 with four segments (3, 4, 5, and 6) with a view from the side of the device with the third segment 5 and fourth segment 6 closest to the viewer and the corner 8 between these segments in the center. The three geometric points comprising the involution 7 between the second segment 4 and third segment 5 are shown in the right hand portion of the figure. The involution 7 proceeds from the third segment 5 via the first geometric point 9 through the second geometric point 10 to the third geometric point 11. This particular involution 7, between the second segment 4 and third segment 5, is a left-handed curve. The three geometric points are non-overlapping. In the current invention, shown in a side view in FIG. 10, the loop connecting point "11" to the next point "11" or point "9" to the next point "9" is on the same plane and does not angle up or down. Each alternating segment directly opposite from the each other and is on the same horizontal plane in the four-segment version of the device. In other words, in a preferred embodiment of the device, there is no angulation in the wire as it moves from one end to another and there are two sides that are above the other two sides (the sides that are above are opposite each other and the sides that are below are opposite each other (the segments 3 and 5) are above and the segments 4 and 6 are below an imaginary horizontal plane that intersects all second geometrical points 10).

Figure 11:
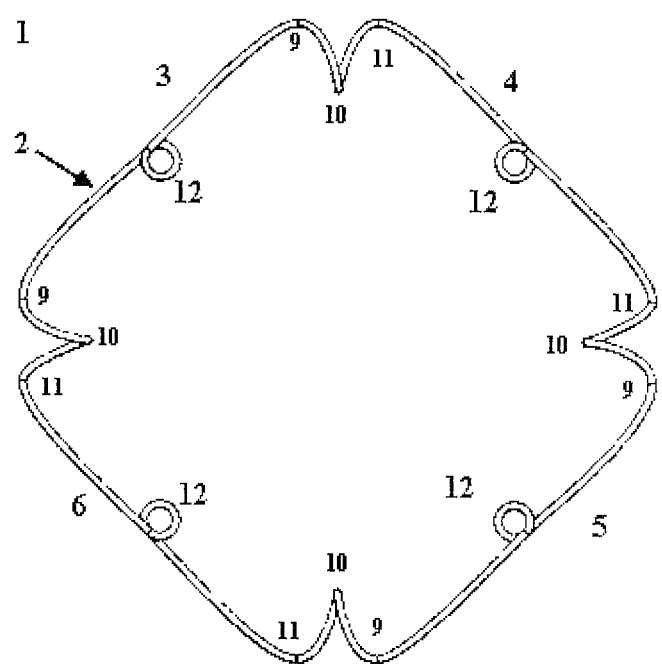
FIG. 11 shows one embodiment of the device 1 that contains positional features 12. In one embodiment, said positional features are spring loops. In one embodiment, said positional features are indentations in the segments. The handedness of each involution 7 alternates after each segment. The loop connecting point "11" to the next point "11" or point "9" to the next point "9" is on the same plane and does not angle up or down. Each alternating segment is directly opposite from the each other and is on the same horizontal plane in the four segment version of the device. In other words, in a preferred embodiment of the device, there is no angulation in the wire as it moves from one end to another and there are two sides that are above the other two sides (the sides that are above are opposite each other and the sides that are below are opposite each other (the segments 3 and 5) are above and the segments 4 and 6 are below an imaginary horizontal plane that intersects all second geometrical points 10).

FIG. 11 shows one embodiment of the device 1 that contains positional features 12. The handedness of each involution 7 alternates after each segment. The loop connecting point "11" to the next point "11" or point "9" to the next point "9" is on the same plane and does not angle up or down. Each alternating segment is directly opposite from the each other and is on the same horizontal plane in the four segment version of the device. In other words, in a preferred embodiment of the device, there is no angulation in the wire as it moves from one end to another and there are two sides that are above the other two sides (the sides that are above are opposite each other and the sides that are below are opposite each other (the segments 3 and 5) are above and the segments 4 and 6 are below an imaginary horizontal plane that intersects all second geometrical points 10).

Figure 12:
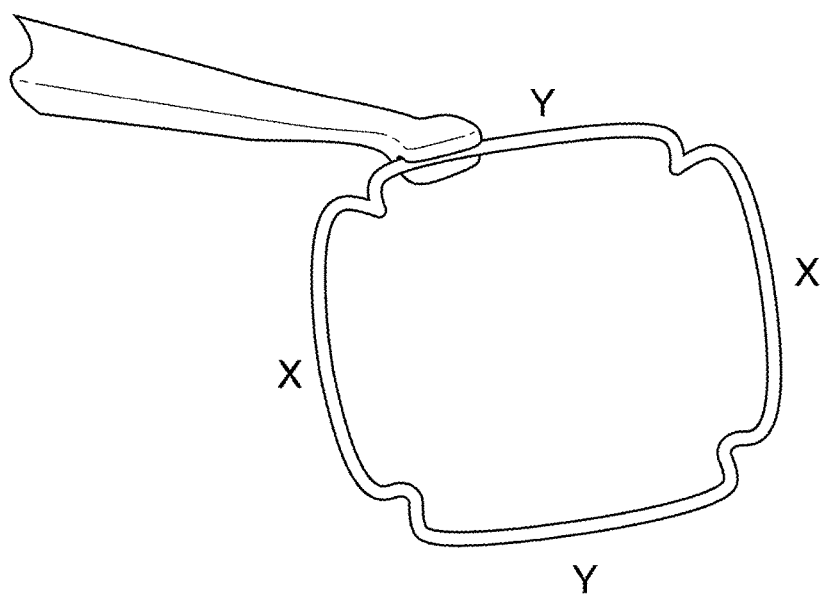
FIG. 12 shows that in the four segments variety of the device 1 has segments across from each other lying in the same plane. The parallel segments are marked here as "x" or "y".

FIG. 12 shows that in the four segments variety of the device 1 has segments across from each other lying in the same plane. The parallel segments are marked here as "x" or "y". The fact that both "x"s are at the same plane and both "y"s are at the same plane will allow for easier insertion in one step as the device is introduced. In this embodiment of the device the configuration ensures that the device will sit parallel to the lens bag during the procedure with minimal tilt and subsequent rubbing of the device on the lens capsule.

Figure 13:
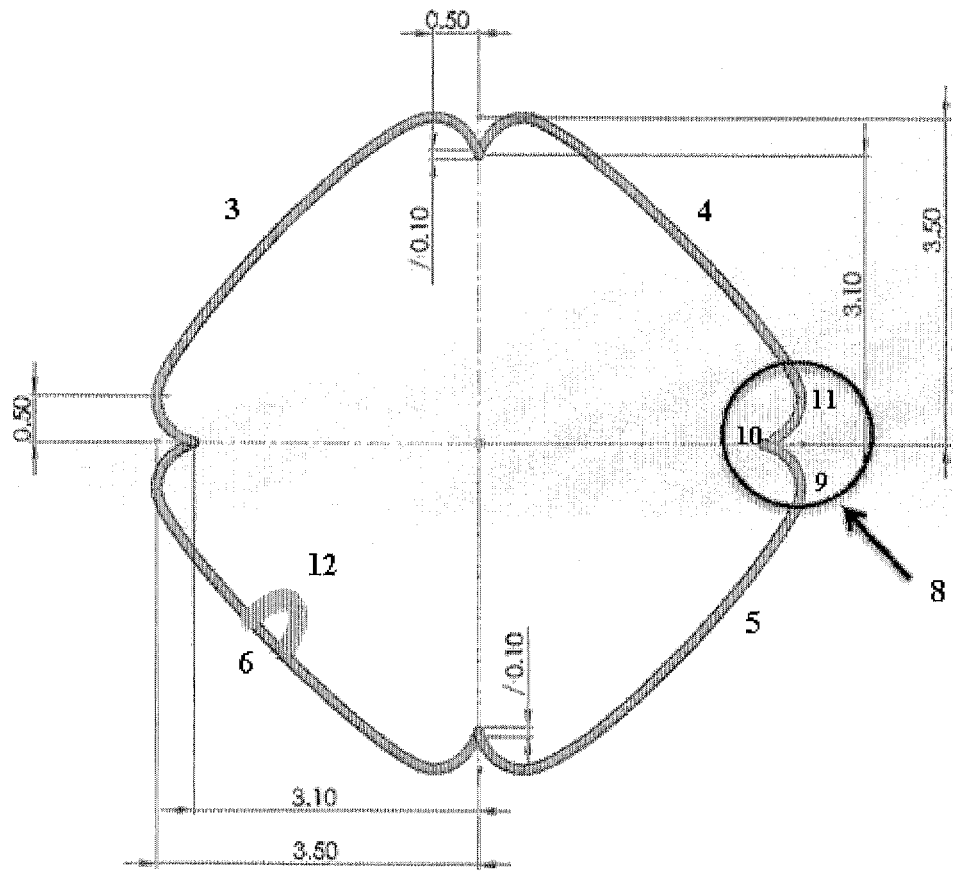
FIG. 13 shows one embodiment of the current invention with four corners (identified as 8) (approximately 90 degrees apart) contain an inset formed by the wire making three geometric points (9, 10, and 11) that are created to ensure no overlapping of segments (as occurs most of the devices described herein) on top of each other (the iris is inserted on top of 11 and below 9 and against 10 and is held in place by the tension the entire ring produces against the iris tissue when in place. The angle of the two segments that form the point "9" is between 30 and 180 degrees similar to the angle formed at point 11. The bend at point "10" is rounded to atraumatically receive the iris. The vertical distance between points 9 and 10 is between 100 and 400 microns. As describe previously, the curve through points 9, 10, and 11 comprise an involution/curve 7. As always, the handedness of the bends alternates at each corner 8.

FIG. 13 shows one embodiment of the current invention with four corners (identified as 8) (approximately 90 degrees apart) contain an inset formed by the wire making three geometric points (9, 10, and 11) that are created to ensure no overlapping of segments (as occurs most of the devices described herein) on top of each other (the iris is inserted on top of 11 and below 9 and against 10 and is held in place by the tension the entire ring produces against the iris tissue when in place. The angle of the two segments that form the point "9" is between 30 and 180 degrees similar to the angle formed at point 11. The bend at point "10" is rounded to atraumatically receive the iris. The vertical distance between points 9 and 10 is between 100 and 400 microns. As describe previously, the curve through points 9, 10, and 11 comprise an involution/curve 7. As always, the handedness of the bends alternates at each corner 8. FIG. 13 also shows an example of a loop positional feature 12.

Figure 14:
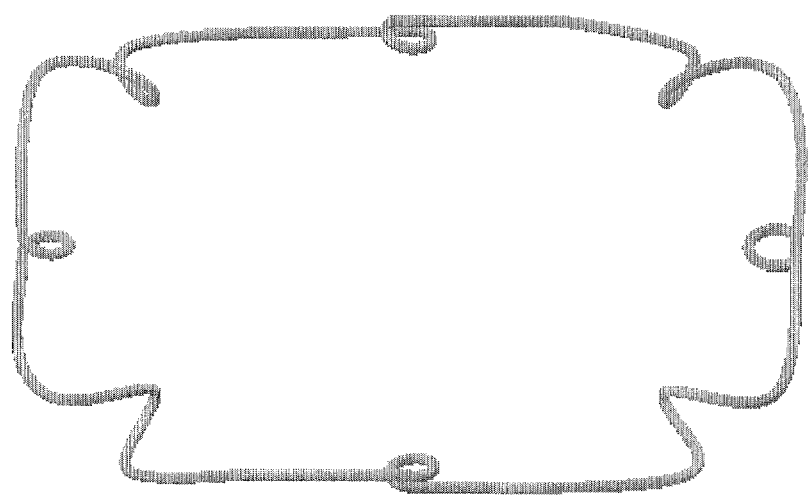
FIG. 14 shows an angled side view of one embodiment of the device, which has four flexible positional features 12 within each segment. In one embodiment, said positional features are spring loops. In one embodiment, said positional features are indentations in the segments.

FIG. 14 shows an angled side view of one embodiment of the device, which has four flexible positional features 12 within each segment.

Figure 15:
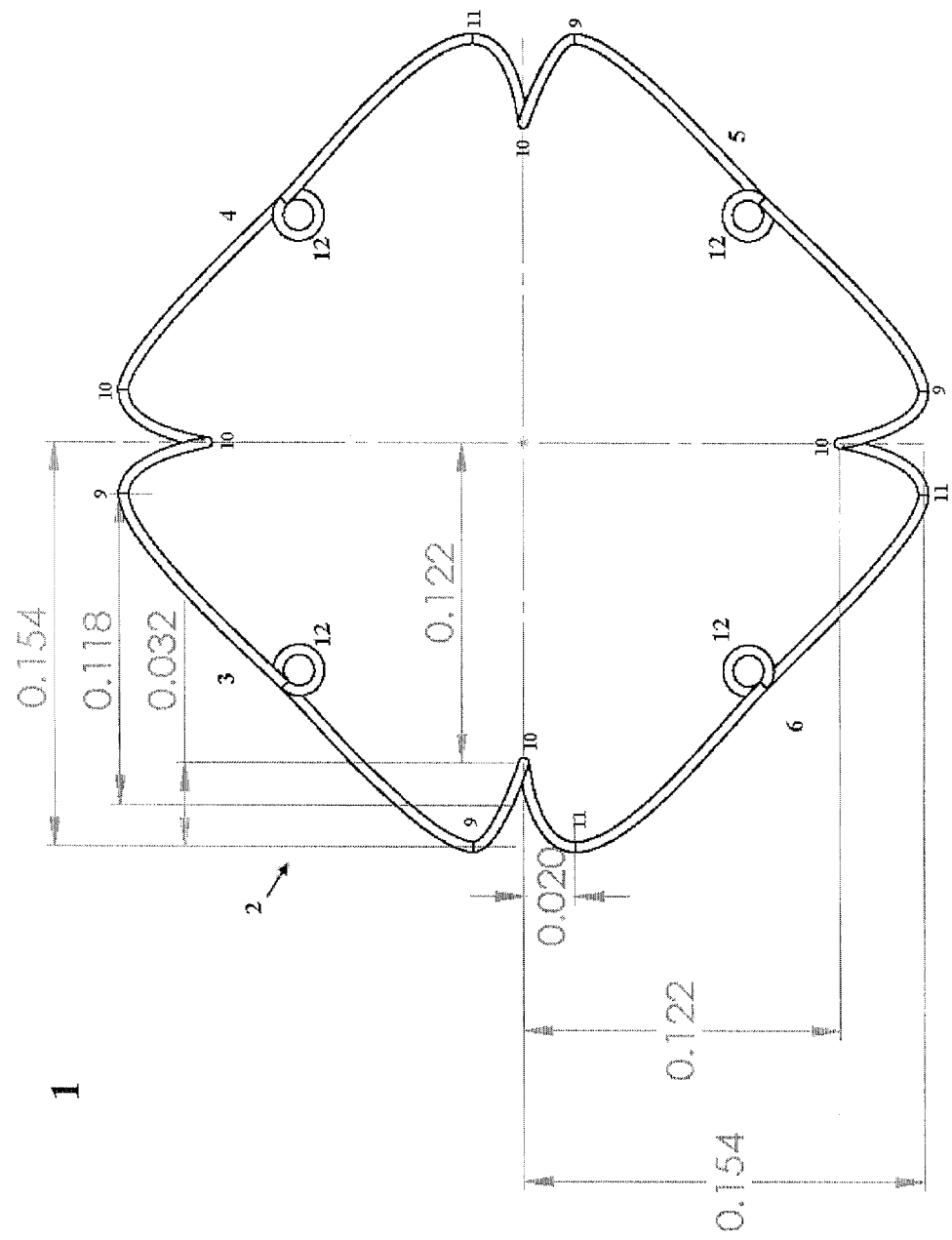
FIG. 15 shows an overhead view of one embodiment of the device, which has four flexible positional features 12 within each segment. In one embodiment, said positional features are spring loops. In one embodiment, said positional features are indentations in the segments. Various dimensions and distances are provided and are in millimeters.

FIG. 15 shows an overhead view of one embodiment of the device, which has four flexible positional features 12 within each segment. Various dimensions and distances are provided and are in millimeters.

Figure 16:
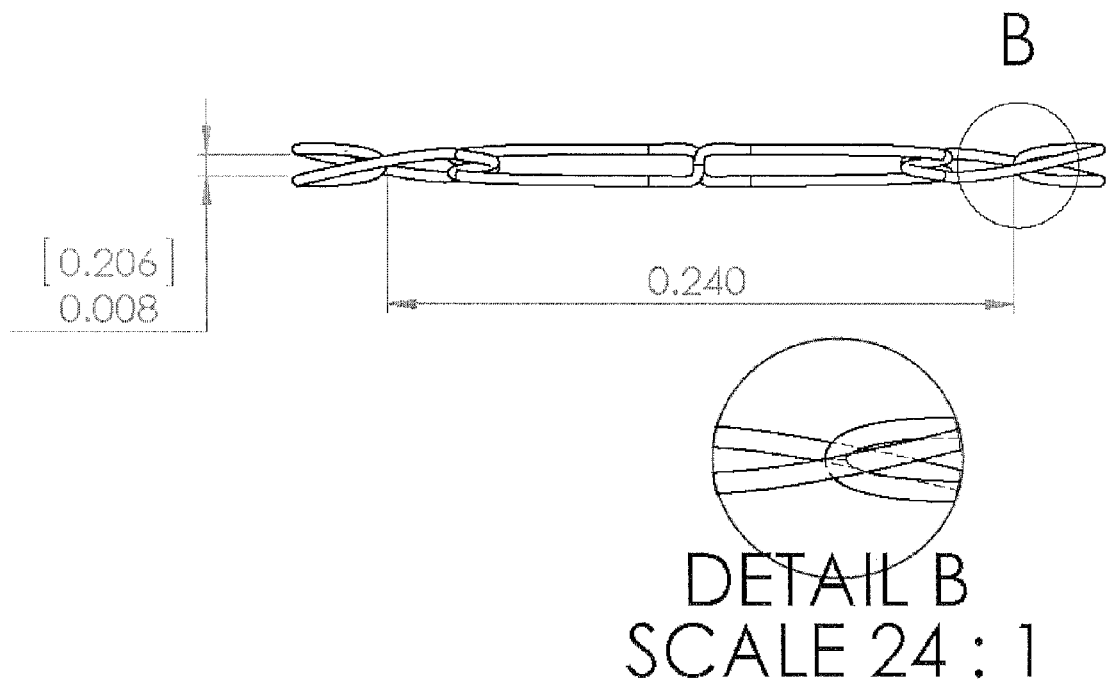
FIG. 16 shows a side view of one embodiment of the device, which has four flexible positional features 12 within each segment. Various dimensions and distances are provided and are in millimeters. The circle B shows a close up of the post-positional spring loop 12 transition to the corner 8/involution 7 between segments.

FIG. 16 shows a side view of one embodiment of the device, which has four flexible positional features 12 within each segment. Various dimensions and distances are provided and are in millimeters. The circle B shows a close up of the post positional loop 12 transition to the corner 8/involution 7 between segments.

Figure 17A:
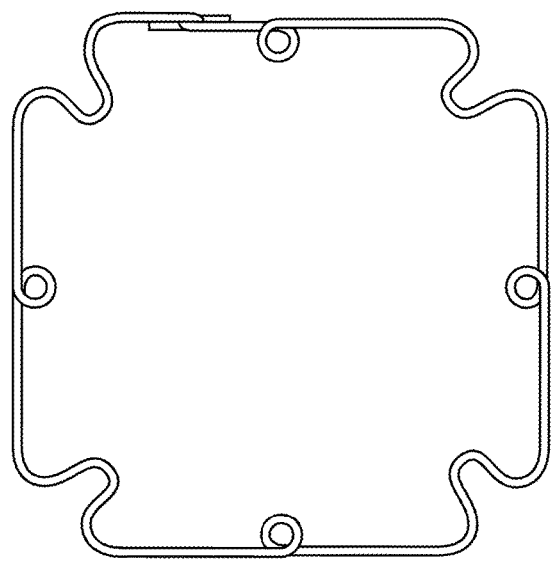
FIG. 17A shows the full device.
Figure 17B:
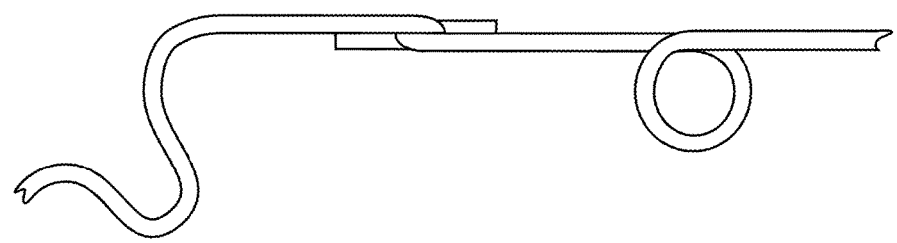
FIG. 17B shows a close up of the side-to-side laser weld that joined the two ends of the nitinol wire to create a closed loop. The welded connection in this location minimizing the stress on the connection and prevents an additional, undesired bend point in the device.
Figure 18:
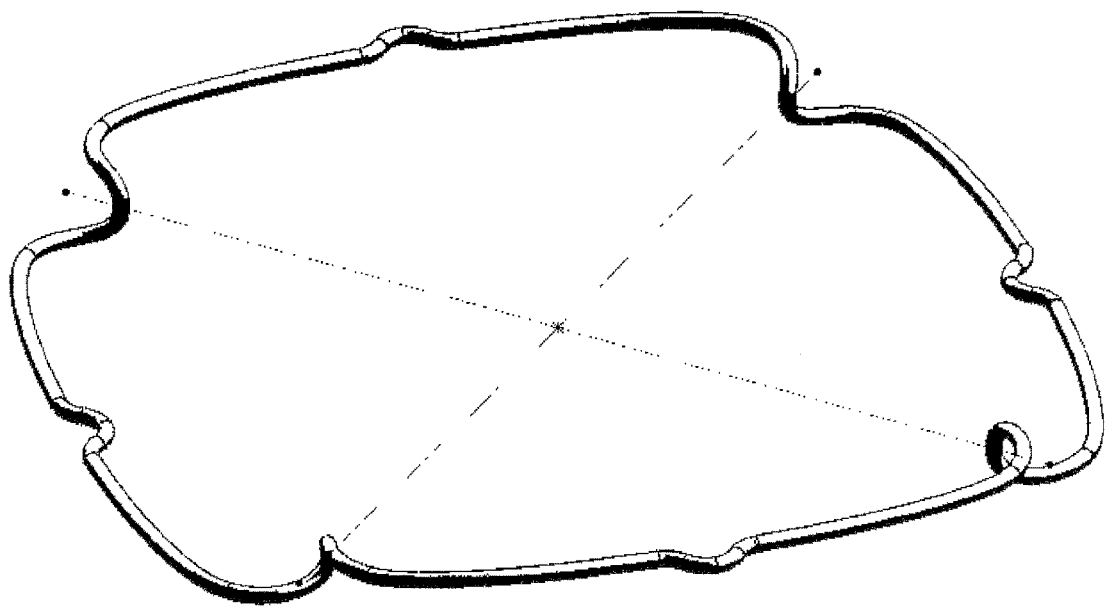
FIG. 18 shows an angled side view of one embodiment of the device wherein the positional features 12 are indentations within the segments.

FIGS. 17 A&B show a manufactured embodiment of the device made from a single nitinol wire. FIG. 17A shows the full device. FIG. 17B shows a close up of the side to side laser weld that joined the two ends of the nitinol wire to create a closed loop. The welded connection in this location minimizing the stress on the connection and prevents an additional, undesired bend point in the device. In other embodiments, the device is a single piece. In one embodiment, the device is made from injection molded single piece.

Figure 19:
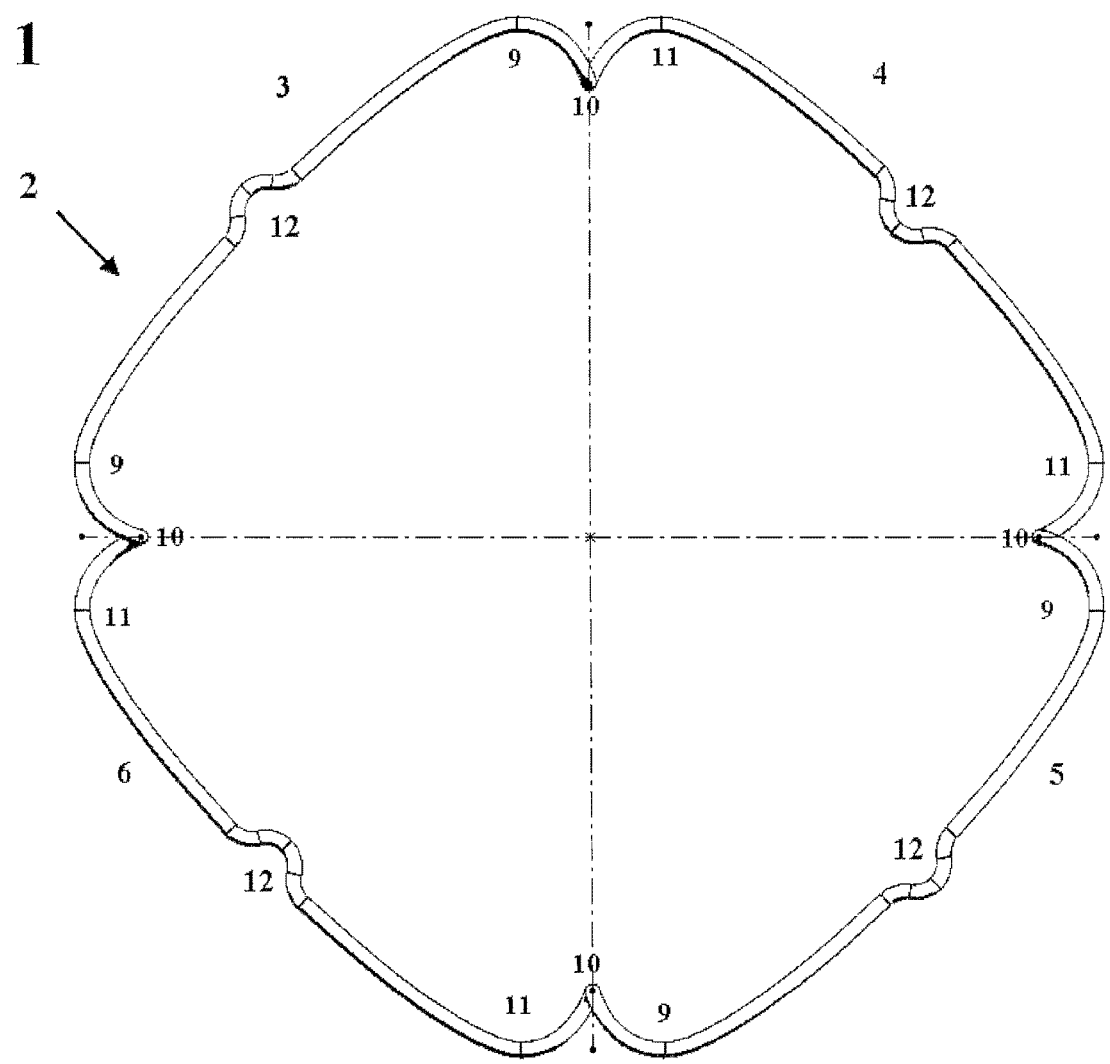
FIG. 19 shows a top view of one embodiment of the device 1, which has four flexible positional features 12, which are indentations/recesses within the segments. The positional features 12 here are recesses rather than loops. The recesses found in segments 3 and 5 are outwardly positioned and the recesses found in segments 4 and 6 are inwardly positioned. Ideally, the device 1 would be positioned within the iris with segments 4 and 6 positioned underneath the iris and segments 3 and 5 positioned above. Positioned in this manner, the positional features 12 may remain accessible for adjustment during the procedure and for easing disengagement of the device 1.
Figure 20:
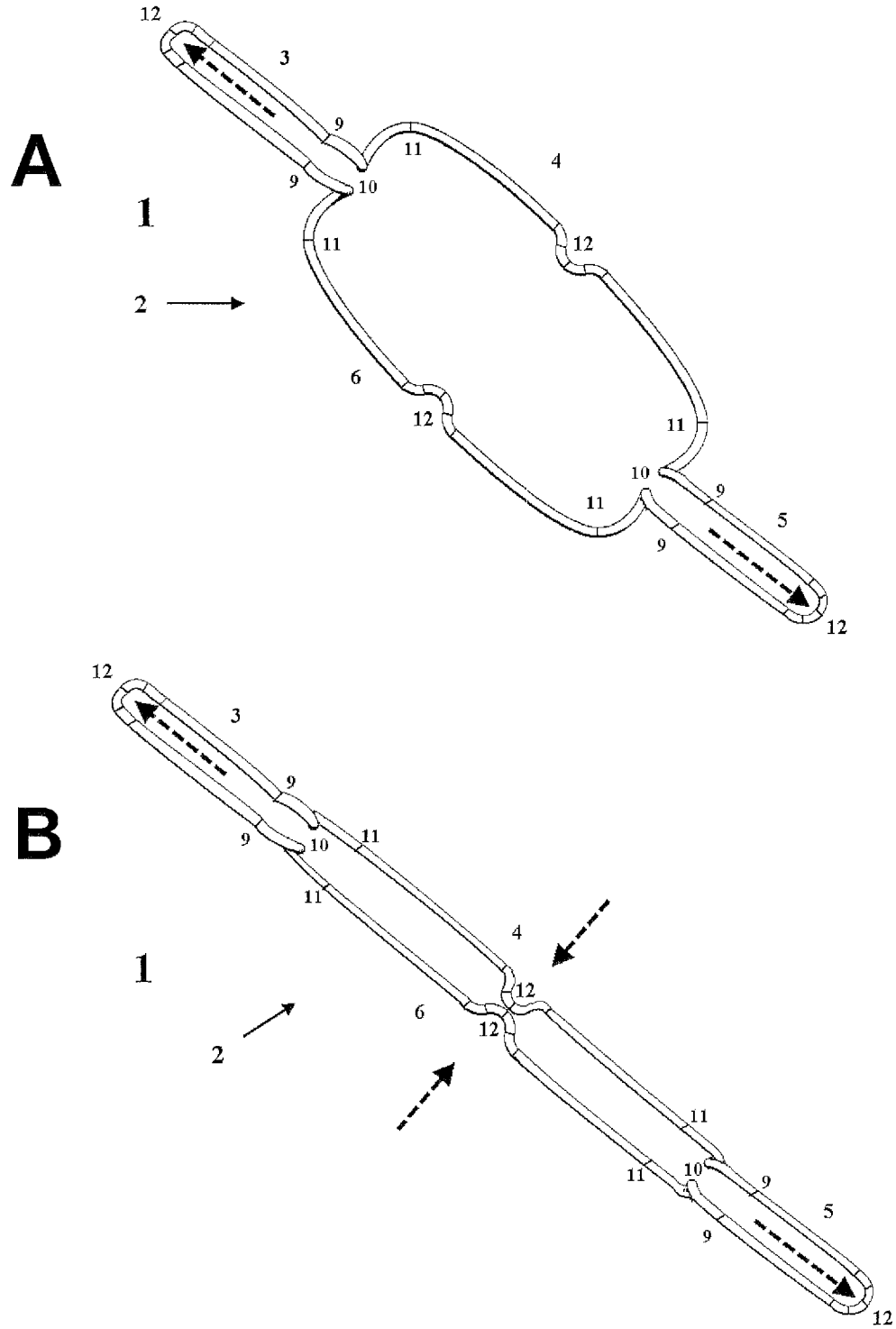
FIG. 20 shows progressive compression of one embodiment of the current invention where the positional features 12 provide flexible points enabling collapse/elongation of the device.
Figure 21:
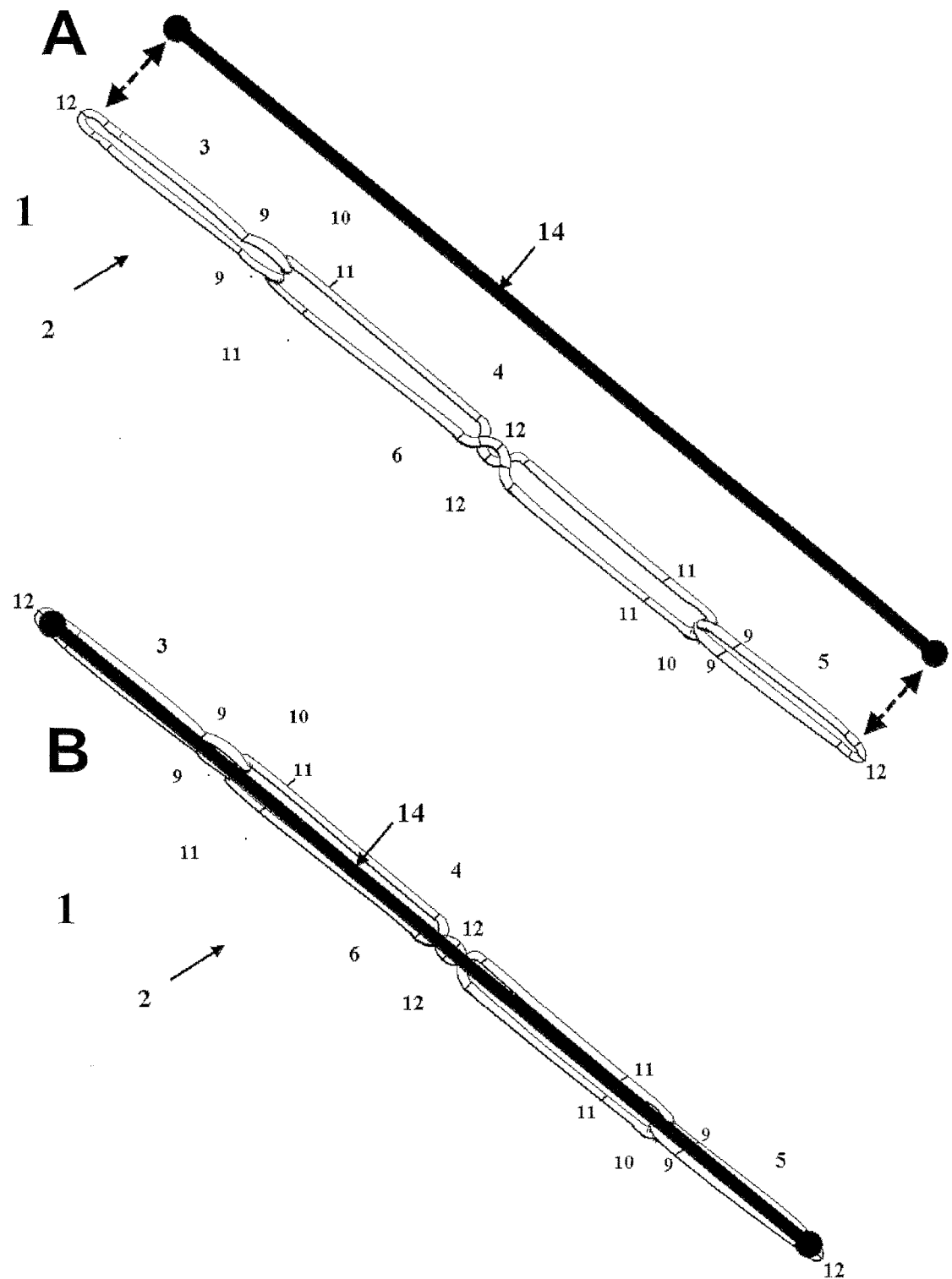
FIGS. 21A&B show the stretched/compressed version of one embodiment of the pupil-expander, which further comprises a device stretching/compression tool 14.
FIG. 21B shows the device stretching/compression tool 14 interfaced with the linearly stretched/compressed ring/loop 2. In one embodiment, said device stretching/compression tool 14 interfaces with said loop at positional features 12 on opposite sides of said device 1 and elongates the device in a substantially linear, stretched/compressed position.
Figure 23:
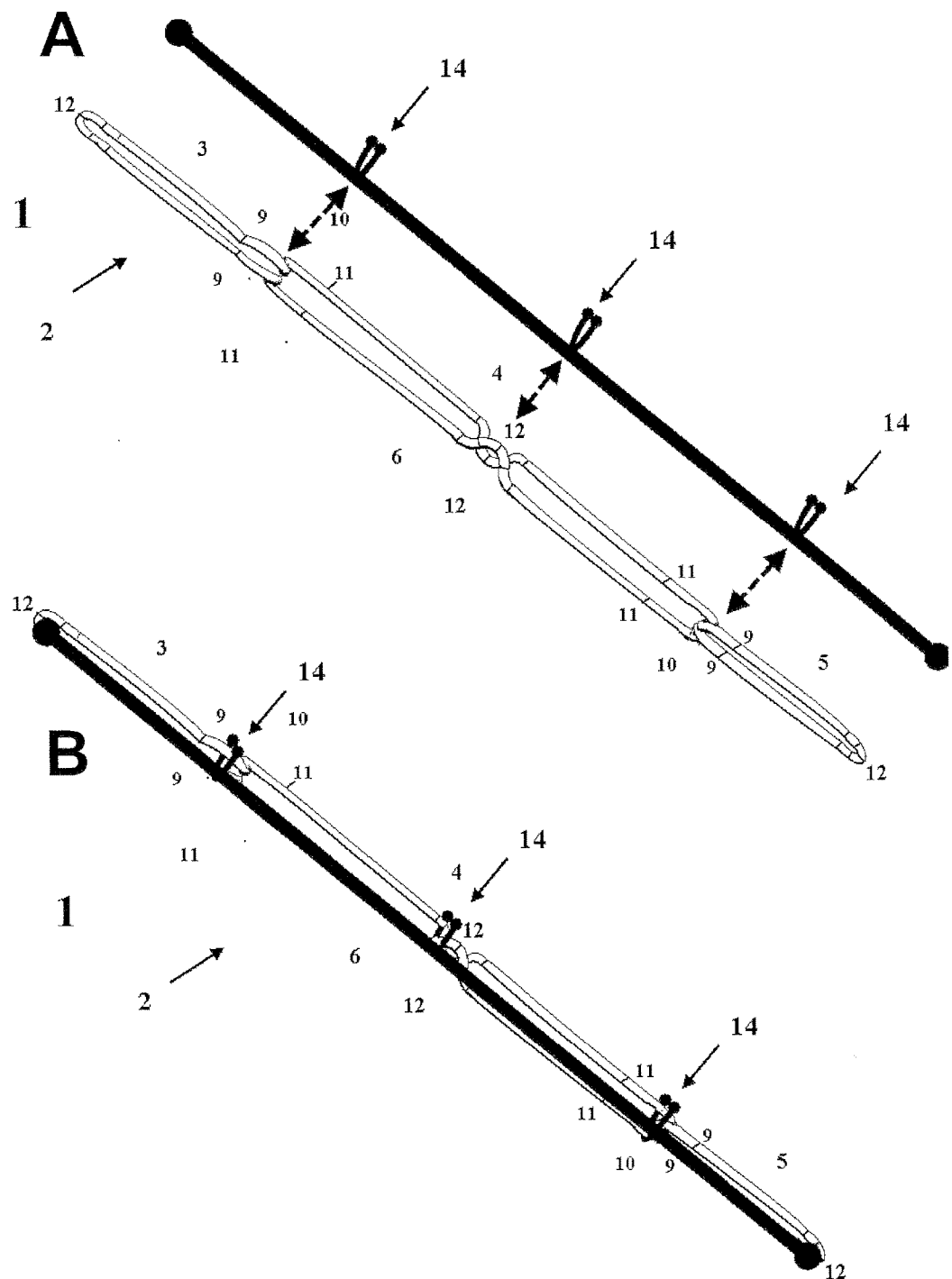
FIGS. 23A&B show the stretched/compressed version of one embodiment of the pupil expander, which further comprises a device stretching/compression tool 14. In one embodiment, said device stretching/compression tool is several clips attached to the central stiff backbone of the device stretching/compression tool 14. The clips attached to the backbone articulate around the stretched/compressed device and keep the stretched/compressed device in a substantially linear position during insertion into the eye.
Figure 24:
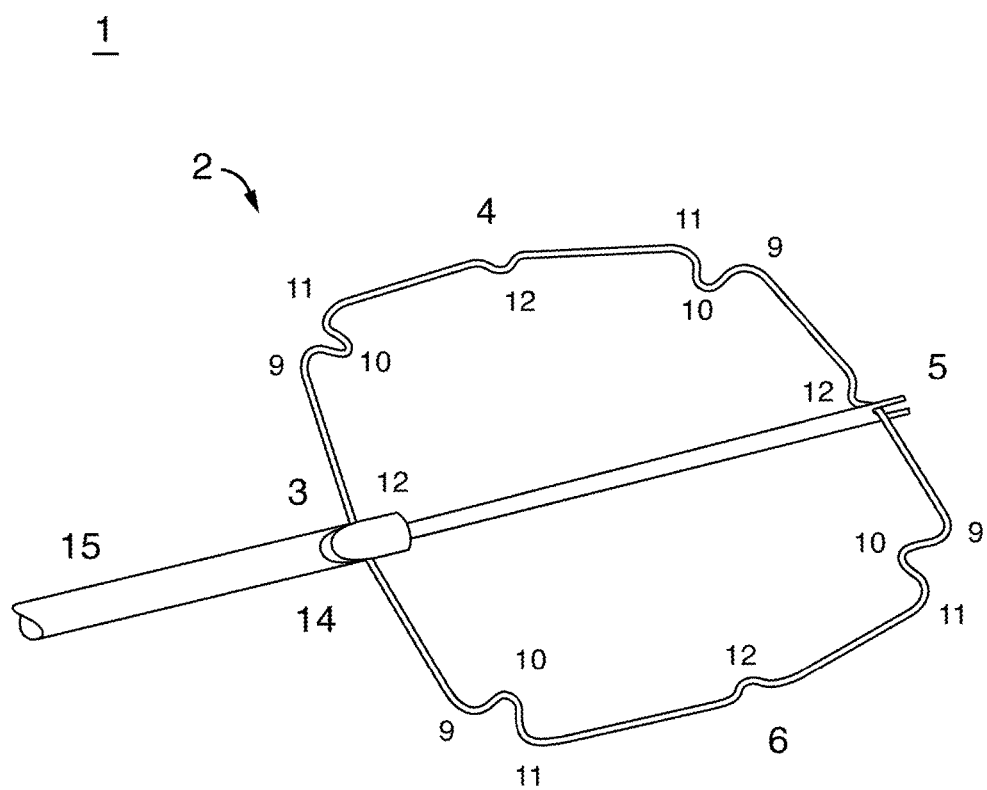
FIG. 24 shows an example of the fully open device 1 positioned upon the insertion tool 15, which comprises a device stretching/compression tool 14. The ring/loop 2 is positioned upon the device stretching/compression tool 14 via the positional features 12.
Figure 25:
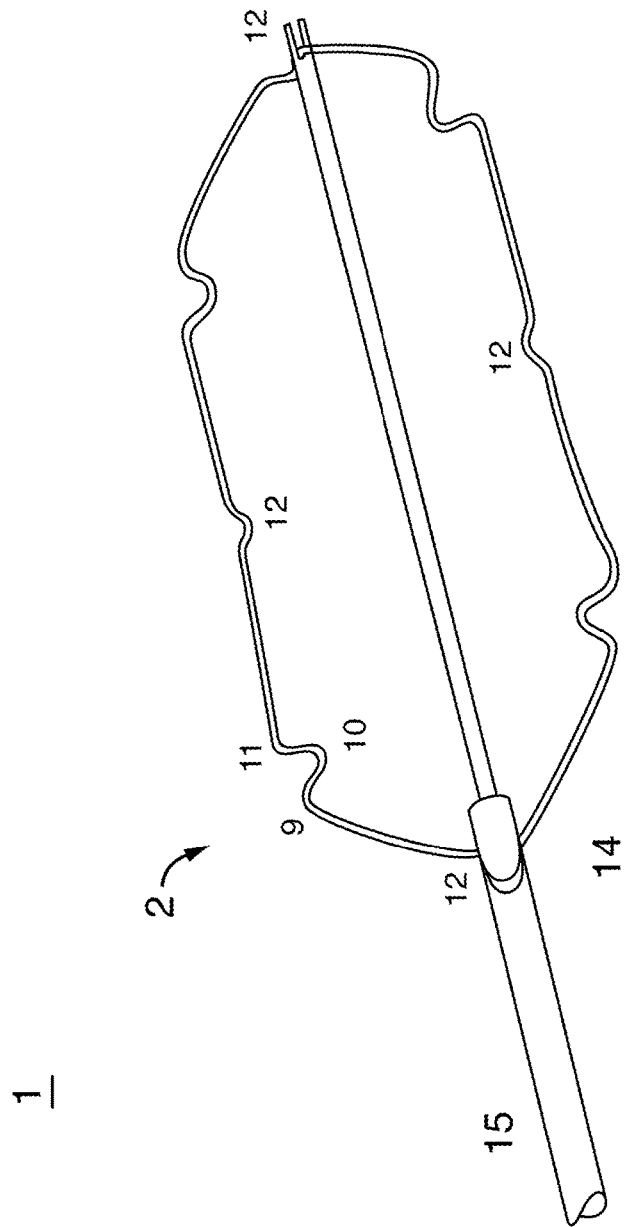
FIG. 25 shows an example of the mid open device 1 positioned upon the insertion tool which comprises a device stretching/compression tool 14, wherein the ring/loop 2 is in the process of being elongated to enable insertion through a small incision. The ring/loop 2 is positioned upon the device stretching/compression tool 14 via the positional features 12.
Figure 26:
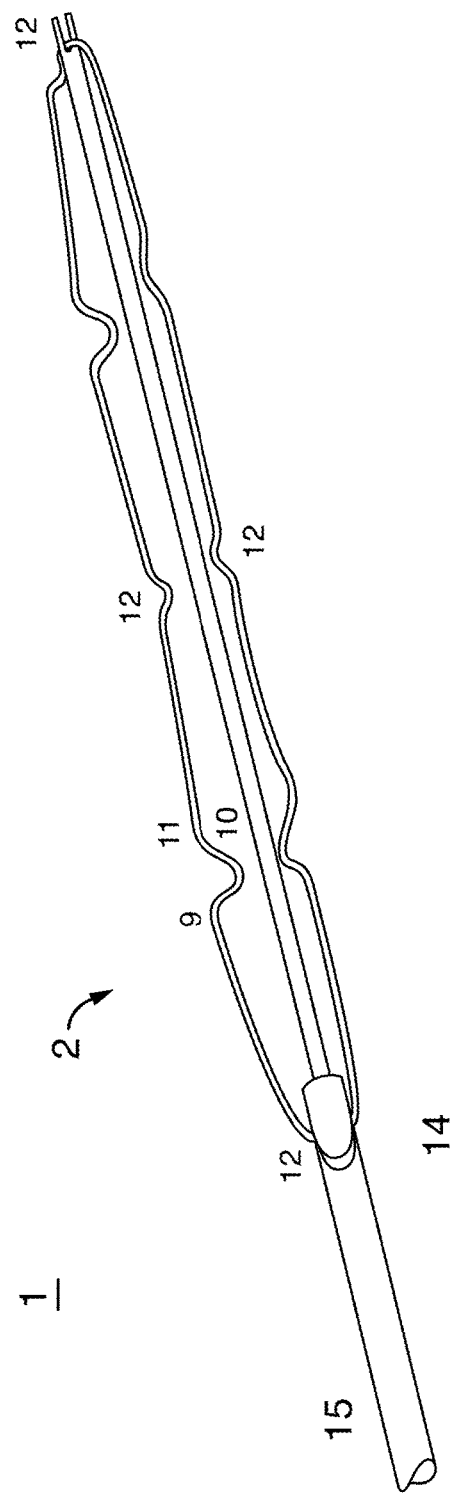
FIG. 26 shows an example of the fully stretched device 1 positioned upon the insertion tool 15 which comprises a device stretching/compression tool 14, wherein the ring/loop 2 is fully elongated to enable insertion through a small incision. The ring/loop 2 is positioned upon the device stretching/compression tool 14 via the positional features 12.
Figure 27:
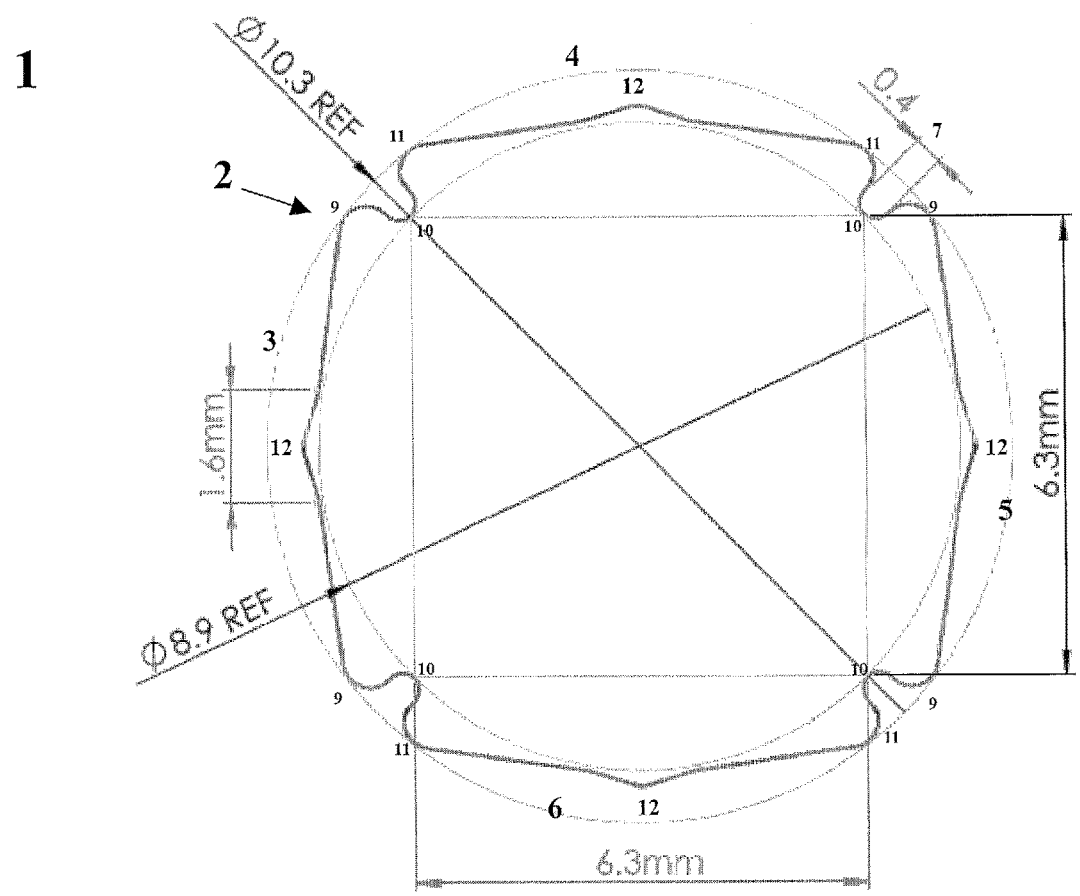
FIG. 27 shows an overhead view of an example of the device 1. In this example, the distance between the geometric points 10 on opposite sides is 10.3 millimeters. In this example, the distance covered on each segment is 6.3 millimeters. In this example, the distance between parallel segments is 8.9 millimeters. In this example, the width of the involution 7 is 0.4 millimeters. In this example, the positional features 12 also include a slightly angled section of the segments. In this example, the slightly angled sections of the segments which apex at the positional feature 12 are angled at 10 degrees relative to the segment.
Figure 28:
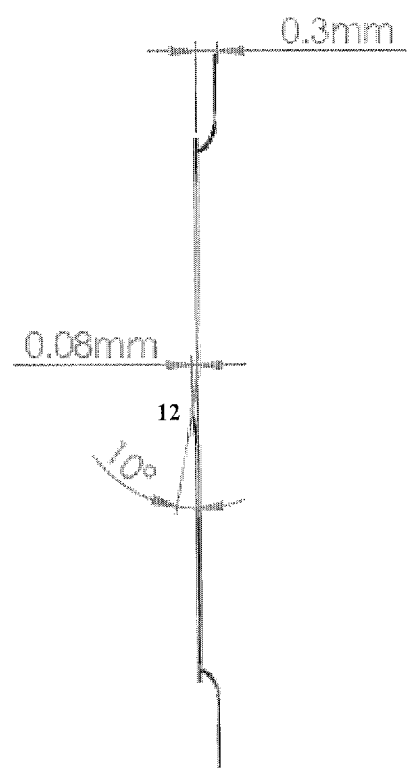
FIG. 28 shows a side view of the device highlighting that the opposite side segments are in the same plane. In this example, the height difference between the segments is 0.3 millimeters. In this example, the mid-point positional feature 12 of each segment of the ring features an extension that is displaced from the plane of that same side so that the feature is higher or lower than the level of the side in which that positional feature 12 is located. In this example, the slightly angled sections of the segments which apex at the positional feature 12 are angled at 10 degrees relative to the segment. In this example, the extension that is displaced from the plane of that same side so that the feature is higher or lower than the level of the side in which that positional feature 12 is located may be 0.08 millimeters distance away from the segment.

FIG. 19 shows an overhead view of one embodiment of the device, which has four flexible positional features 12 within each segment. The positional features 12 here are recesses rather than loops. FIG. 20 shows progressive compression of one embodiment of the current invention where the positional features 12 provide flexible points enabling collapse/elongation of the device. FIG. 20A shows an initial phase of compression of the device wherein the positional features 12 within segments 3 and 5 are pulled in opposite directions and the device collapses and segments 4 and 6 move closer together. FIG. 20B shows wherein the positional features 12 on segments 4 and 6 are essentially touching or overlapping and geometric points 10 on the end of segment 3 are adjacent and geometric points 10 on the end of segment 5 are adjacent. In one embodiment, said pupil expander further comprises a device stretching/compression tool 14, see FIGS. 21A&B. FIGS. 21A&B show the stretched/compressed version of one embodiment of the pupil expander which further comprises a device stretching/compression tool 14. FIG. 21A shows a stretched/compressed embodiment of the current invention with the device stretching/compression tool next to the linearly stretched/compressed ring/loop 2 with arrows indicating how it will articulate with the linearly stretched/compressed ring/loop 2. FIG. 21B shows the device stretching/compression tool 14 interfaced with the linearly stretched/compressed ring/loop 2. In one embodiment, said device stretching/compression tool 14 interfaces with said loop at positional features 12 on opposite sides of said device 1 and elongates the device in a substantially linear, stretched/compressed position.

Thus, specific compositions and configurations of ocular tissue expansion ring have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

REFERENCES

1. Dusek, V. "Extension Ring For Eyeball Tissue," United States Patent Application Publication Number US 2012-0289786 A1, application Ser. No. 13/291,946, filed Nov. 8, 2011. (published Nov. 15, 2012).
2. Chang, D. F. (2008) "Use of Malyugin pupil expansion device for intraoperative floppy-iris syndrome: Results in 30 consecutive cases," J. Cataract. Refract. Surg. 34(5), 835-841.
3. Rauen, M. and Oetting, T. (2010) "Partial retraction of Malyugin pupil expansion device to improve safety during ring removal," J. Cataract. Refract. Surg. 36(3), 522-523.
4. Christensen, J. M. and Colvard, D. M. "Ophthalmic Structure," U.S. Pat. No. 8,439,833, application Ser. No. 13/275,685, filed Oct. 18, 2011. (issued May 14, 2013).
5. Graether, J. M. "Pupil Expander And Method Of Using The Same," U.S. Pat. No. 5,267,553, application Ser. No. 07/836,361, filed Feb. 18, 1992. (issued Dec. 7, 1993).
6. Sussman, G R. et al. "Devices, Systems, And Methods For Pupil Expansion," United States Patent Application Publication Number US 2013-0267988 A1, application Ser. No. 13/438,881, filed Apr. 4, 2012. (published Oct. 10, 2013).

7. Reynard, M. "Pupil Dilation System," U.S. Pat. No. 8,496,583, application Ser. No. 13/668,229, filed Nov. 3, 2012. (issued Jul. 30, 2013).
8. Bhattacharjee, S. (2014) "Pupil-expansion ring implantation through a 0.9 mm incision," *J. Cataract Refract. Surg.* 40(7), 1061-1067.

We claim:

1. A device comprising:
   a compressible polygon elastomer loop with an even number of sides having alternating side segments connected by a plurality of non-overlapping involutions,
   wherein said non-overlapping involutions alternate in handedness when adjacent,
   wherein every other segment is within a same geometrical plane,
   wherein at least one segment contains at least one positional feature, and
   wherein said positional feature includes at least one of the following: is at a midpoint of each segment; alternates on adjacent segments in being curved inwards toward the center of the device; and further comprises an extension that is displaced from the same geometrical plane of the-segment containing said at least one positional feature; wherein said feature is higher or lower than a level of the segment in which said positional feature is located.

2. The device of claim 1, wherein said loop comprises at least four segments.

3. The device of claim 2, wherein each of said segments is straight between said involutions.

4. The device of claim 2, wherein said every other segment are at 90-degree angles.

5. The device of claim 1, wherein said involutions comprises a continuous curve through three geometric points that are not overlapping with said segments.

6. The device of claim 1, wherein said positional feature is selected from the group consisting of: a flexible recess and a spring loop.

7. The device of claim 1, wherein said loop is made from the material selected from the group consisting of: a polymer; nitinol; and a medical grade metal alloy.

8. The device of claim 7, wherein said polymer is selected from the group consisting of: medical grade silicone, hydrophobic acrylic, hydrophilic acrylic, and other common medical grade polymers.

9. The device of claim 1, wherein said loop further comprises a stiffened polymer backbone with a flexible coating.

10. A method of inserting a pupil-expanding device into an eye comprising:
    a) providing a device comprising:
       a compressible polygon elastomer loop with an even number of sides having alternating side segments connected by a plurality of non-overlapping involutions,
       wherein said non-overlapping involutions alternate in handedness when adjacent,
       wherein every other segment is within a same geometrical plane,
       wherein at least one segment contains at least one positional feature, and
       wherein said positional feature includes at least one of the following: is at a midpoint of each segment; alternates on adjacent segments in being curved inwards toward the center of the device; and further comprises an extension that is displaced from the same geometrical plane of the segment containing said at least one positional feature; wherein said feature is higher or lower than a level of the segment in which said positional feature is located;
    b) stretching said device linearly;
    c) making a cornea or scleral incision such that a connection is made to an anterior chamber of an eye;
    d) inserting said device into and through said incision;
    e) positioning said device in the anterior chamber of the eye;
    f) manipulating said device into a non-stretched form; and
    f) inserting said device within a pupil and against iris tissue such that it expands a pupil opening.

11. The method of claim 10, wherein said manipulating said device into a non-stretched form comprises removal of a device stretching/compression tool from said device.

12. The method of claim 10, wherein said insertion uses an insertion tool to spread opposing segments apart from each other so that the device is elongated and in this process stretched when non-engaged sides collapse towards each other as parts engaged by said insertion tool are spread apart from each other.

13. The method of claim 10, wherein said manipulating said device into a non-stretched form comprises pulling segments of the device apart.

14. The method of claim 10, wherein said insertion comprises expanding said device such that opposite segments are parallel and then placing a first, lower segment underneath the edge of the pupil such that adjacent upper segments articulate above an edge of the pupil, and subsequent manipulation of another lower segment beneath the edge of the pupil.

15. A method of removing a pupil-expanding device from an eye comprising:
    a) having a pupil-expanding device positioned within the pupil of the eye, wherein said a device comprises:
       a compressible polygon elastomer loop with an even number of sides having alternating side segments connected by a plurality of non-overlapping involutions,
       wherein said non-overlapping involutions alternate in handedness when adjacent,
       wherein every other segment is within a same geometrical plane,
       wherein at least one segment contains at least one positional feature, and
       wherein said positional feature includes at least one of the following: is at a midpoint of each segment; alternates on adjacent segments in being curved inwards toward the center of the device; and further comprises an extension that is displaced from the same geometrical plane of the segment containing said at least one positional feature; wherein said feature is higher or lower than a level of the segment in which said positional feature is located;
    b) articulating segments from underneath an edge of the pupil; and
    c) drawing said device through a surgical opening out of the eye.

* * * * *